US011058106B2

(12) United States Patent
Rowley et al.

(10) Patent No.: US 11,058,106 B2
(45) Date of Patent: Jul. 13, 2021

(54) READY-TO-PRINT CELLS AND INTEGRATED DEVICES

(71) Applicant: ROOSTERBIO, INC., Frederick, MD (US)

(72) Inventors: Jonathan Allen Rowley, Walkersville, MD (US); Lye Theng Lock, Frederick, MD (US)

(73) Assignee: ROOSTERBIO, INC., Frederick, MD (US)

( * ) Notice: Subject to any disclaimer, the term of this patent is extended or adjusted under 35 U.S.C. 154(b) by 11 days.

(21) Appl. No.: 15/311,018

(22) PCT Filed: May 12, 2015

(86) PCT No.: PCT/US2015/030260
§ 371 (c)(1),
(2) Date: Nov. 14, 2016

(87) PCT Pub. No.: WO2015/175457
PCT Pub. Date: Nov. 19, 2015

(65) Prior Publication Data
US 2017/0079262 A1    Mar. 23, 2017

Related U.S. Application Data

(60) Provisional application No. 61/992,184, filed on May 12, 2014.

(51) Int. Cl.
| | | |
|---|---|---|
| *C12N 5/0775* | (2010.01) | |
| *C12N 1/04* | (2006.01) | |
| *A01N 1/02* | (2006.01) | |
| *C12N 5/00* | (2006.01) | |
| *A61L 27/38* | (2006.01) | |
| *A61L 27/36* | (2006.01) | |
| *A61L 27/26* | (2006.01) | |
| *C12N 5/077* | (2010.01) | |
| *A61L 27/16* | (2006.01) | |
| *B33Y 10/00* | (2015.01) | |

(52) U.S. Cl.
CPC ......... *A01N 1/0231* (2013.01); *A01N 1/0221* (2013.01); *C12N 1/04* (2013.01); *C12N 5/0663* (2013.01); *B33Y 10/00* (2014.12); *C12N 2533/74* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,496,722 A * | 3/1996 | Goodwin | C12M 27/10 |
| | | | 435/1.1 |
| 5,798,113 A * | 8/1998 | Dionne | A61K 9/0024 |
| | | | 424/422 |
| 6,387,369 B1 | 5/2002 | Pittenger et al. | |
| 6,712,963 B2 | 3/2004 | Schick | |
| 7,051,654 B2 | 5/2006 | Boland et al. | |
| 7,101,704 B1 | 9/2006 | Mosca | |
| 7,153,500 B2 | 12/2006 | Qasba et al. | |
| 2003/0017549 A1* | 1/2003 | Owens | C12N 15/85 |
| | | | 435/69.7 |
| 2005/0129730 A1* | 6/2005 | Pang | A61L 27/24 |
| | | | 424/423 |
| 2006/0257378 A1* | 11/2006 | Crumpler | A61K 9/0019 |
| | | | 424/93.7 |
| 2007/0020754 A1 | 1/2007 | Yuge et al. | |
| 2008/0070304 A1* | 3/2008 | Forgacs | C12N 5/0062 |
| | | | 435/397 |
| 2009/0130756 A1 | 5/2009 | Klann et al. | |
| 2011/0250688 A1* | 10/2011 | Hasan | C12N 5/0062 |
| | | | 435/395 |
| 2012/0076854 A1 | 3/2012 | Hope et al. | |
| 2012/0219572 A1* | 8/2012 | Prockop | A61P 29/00 |
| | | | 424/184.1 |
| 2014/0342346 A1 | 11/2014 | Ando et al. | |

FOREIGN PATENT DOCUMENTS

| | | | | |
|---|---|---|---|---|
| JP | 2013110988 A | | 6/2013 | |
| WO | 2005037984 A1 | | 4/2005 | |
| WO | 2010143747 A1 | | 12/2010 | |
| WO | 2012158899 A1 | | 11/2012 | |
| WO | 2013077424 A1 | | 5/2013 | |
| WO | WO 15/066705 | * | 5/2015 | ............... B01L 9/02 |

OTHER PUBLICATIONS

Frantz. C. et al. Journal of Cell Science. 2010. 123: 4195-4200. (Year: 2010).*
McGuigan, AP et al. PLoS One. 2008. 3(5): e2258. 11 pages. (Year: 2008).*
Spalding, KL et al. Nature. Jun. 5, 2008. 453: 783-787. (Year: 2008).*
Lee, KY et al. Prog. Polym. Sci. Jan. 2012. 37(1): 106-126. Author manuscript. 45 pages. (Year: 2012).*
Janeczek, K et al. PLoS One. Oct. 2012. 7(1): e46842. 16 pages. (Year: 2012).*
Frontini, A et al. Cell Cycle. Aug. 1, 2012. 11(15): 2765-2766. (Year: 2012).*
Wilson et al, Biotechnology and Bioengineering, Mar. 2014, vol. 111. No. 3, pp. 618-631. (Year: 2014).*
Pogozhykh et al, PLoS One, 2015, vol. 10, Iss 10, e0139834 (16 pages) (Year: 2015).*
Ginis et al, Tissue Engineering Pt C, 2012, 18(6): 453-463. (Year: 2012).*

(Continued)

*Primary Examiner* — Allison M Fox
(74) *Attorney, Agent, or Firm* — Meunier Carlin & Curfman LLC

(57) ABSTRACT

Disclosed herein are compositions, devices, and methods that provide cellular materials in ready to use formats for experimental, therapeutic, and tissue engineering protocols. For example, compositions containing frozen or non-frozen cell present as aggregates are disclosed. Also disclosed a compositions containing cellular materials that after storage are suitable for dispersion, e.g. by 3D printing. Also disclosed is a kit for producing bioink compositions. Also disclosed is a closed system device comprising a cell material composition described herein.

10 Claims, 18 Drawing Sheets

(56) References Cited

OTHER PUBLICATIONS

Pravdyuketal, Cryobiology, 2013, 66: 215-222. (Year: 2013).*
Malpique et al, Tissue Engineering Pt C, 2010, vol. 16, No. 6, pp. 1-13. (Year: 2010).*
Zhang et al, Biomed Microdevices, 2010, vol. 12, pp. 89-96. (Year: 2010).*
Office Action issued for Chinese Application No. 201580027934, dated Dec. 3, 2019.
Office Action issued for Japanese Application No. 2017-512651, dated Mar. 10, 2020.
Office Action issued for Japanese Application No. 2017-512651, dated Apr. 2, 2019.
Faulkner-Jones, Alan, et al. "Development of a valve-based cell printer for the formation of human embryonic stem cell spheroid aggregates." Biofabrication 5.1 (2013): 015013.
Ginis, Irene, Borislava Grinblat, and Mitchell H. Shirvan. "Evaluation of bone marrow-derived mesenchymal stem cells after cryopreservation and hypothermic storage in clinically safe medium." Tissue Engineering Part C: Methods 18.6 (2012): 453-463.
Communication Pursuant to Article 94(3) EPC, issued for Application No. 15792,516.5, dated Apr. 18, 2019.
Communication Pursuant to Article 94(3) EPC, issued for Application No. 15792,516.5, dated Oct. 11, 2019.
Communication Pursuant to Article 94(3) EPC, issued for Application No. 15792,516.5, dated Jul. 17, 2020.
Communication Pursuant to Article 94(3) EPC, issued for Application No. 15792,516.5, dated Oct. 22, 2018.
Clarke, et al., "Biopreservation Economics 101.", BioLife Solutions, Corporate Tutorial. May 24, 2010, [Retrieved on Aug. 3, 2015]. Retrieved from the Internet: <URL:http://biolifesolutions.com/biopreservation-media/2010_ISCT_BioLife_Tutorial_Presentation.pdf.
Malpique, et al., "Cryopreservation of Adherent Cells: Strategies to Improve Cell Viability and Function after thawing". Tissue Eng Part C Methods. Sep. 2009, vol. 15, No. 3; pp. 373-386.
Massie, IR. Development of an Optimised Cryopreservation Protocol for Encapsulated Liver Cell Spheroids: Towards Delivery of a Bioartificial Liver. Doctoral thesis, University of College London. 2012 [Retrieved on Aug. 3, 2015]. Retrieved from the Internet:URL:http://discovery.ucl.ac.uk/1346470/; paragraphs 2.2.1, 2.2.1.1, 2.9.2.
International Search Report and Written Opinion issued in Application No. PCT/US15/30260 dated Sep. 30, 2015.
International Preliminary Report on Patentability Opinion issued in Application No. PCT/US15/30260 dated Nov. 24, 2016.
Sart, S., et al. Cryopreservation of Pluripotent Stem Cell Aggregates in Defined Protein-Free Formulation. Biotechnol Prog. Jan. 2013, vol. 29, No. 1; pp. 143-153.
Zhou, et al., Development Potential of Mouse Embryos Reconstructed from Metaphase Embryonic Stem Cell Nuclei. Biol Reprod. Aug. 2001, vol. 65, No. 2; pp. 412-419.

Friedenstein et al., "The Development of Fibroblast Colonies in Monolayer Cultures of Guinea-Pig Bone Marrow and Spleen Cells", 1970 Cell Tissue Kinet. 3:393-403.
Castro-Malaspina, et al., "Characterization of human bone marrow fibroblast colony-forming cells (CFU-F) and their progeny", 1980 Blood 56:289-301.
Beresford et al., "Evidence for an inverse relationship between the differentiation of adipocytic and osteogenic cells in rat marrow stromal cell cultures",1992 J. Cell Sci. 102:341-351.
Prockop, "Marrow stromal cells as stem cells for nonhematopoietic tissues", 1997, Science 276:71-74.
Wakitani et al, "Myogenic cells derived from rat bone marrow mesenchymal stem cells exposed to 5-azacytidine", 1995, Muscle Nerve 18:1417-1426.
Azizi et al., "Engraftment and migration of human bone marrow stromal cells implanted in the brains of albino rats—similarities to astrocyte grafts", 1998 Proc. Natl. Acad. Sci. USA 95:3908-3913.
Kopen et al., "Marrow stromal cells migrate throughout forebrain and cerebellum, and they differentiate into astrocytes after injection into neonatal mouse brains", 1999 Proc. Natl. Acad. Sci. USA 96:10711-10716.
Chopp et al., "Spinal cord injury in rat: treatment with bone marrow stromal cell transplantation", 2000 Neuroreport 11:3001-3005.
Woodbury et al., "Adult Rat and Human Bone Marrow Stromal Cells Differentiate Into Neurons", 2000 Neuroscience Res. 61:364-370.
Horwitz et al., "Transplantability and therapeutic effects of bone marrow-derived mesenchymal cells in children with osteogenesis imperfecta", 1999 Nat. Med. 5:309-313.
Caplan, et al., "Mesenchymal Stem Cells and Gene Therapy", Clin. Orthoped. 2000, 379:S67-57.
Bartosh, et al., "Aggregation of human mesenchymal stromal cells (MSCs) into 3D spheroids enhances their anti-inflammatory properties", PNAS 2010 107(31):13724-13729.
Malda, J, et al, "25th anniversary article: Engineering hydrogels for bio fabrication", Adv. Mater. 2013, 25, 5011-5028.
Murphy, et al, "Evaluation of hydrogels for bio-printing applications", J Biomed Mater Res Part A 2013:101A:272-284.
Guvendiren et al., "Engineering synthetic hydrogel microenvironments to instruct stem cells", Current Opinion in Biotechnology 2013, 24:841-846.
Pegg, "Viability assays for preserved cells, tissues, and organs". Cryobiology 1989, 26(3): 212-231.
Office Action issued for Chinese Application No. 201580027934.7, dated Nov. 4, 2020.
Decision to grant a patent issued for Japanese Application No. 2017-512651, dated Nov. 24, 2020.
Office Action issued for Korean Application No. 10-2016-7034122, dated Dec. 29, 2020.
Communication Pursuant to Article 94(3) EPC, issued for European Application No. 15792516.5, dated Oct. 22, 2018, 3 pages.
First Examination Report issued for Australian Application No. 2015259373, dated May 17, 2018, 5 pages.
Extended European Search Report issued for Application No. EP15792516, dated Nov. 11, 2017.

* cited by examiner

CRYOPRESERVED

1 DAY FUSION

1 DAY ADHESION

6 DAY ADHESION

| | ALGINATE | GELLING FORMULATION | CONSISTENCY | TACKINESS |
|---|---|---|---|---|
| A | 2% HIGH G | 2.5 mg/ml CaSO4 | 4 | 4 |
| B | 2% HIGH G | 1.25 mg/ml CaSO4 | 2-3 | 5 |
| C | 2% HIGH G | 0.63 mg/ml CaSO4 | 1 | 3 |
| D | 2% HIGH M | 2.5 mg/ml CaSO4 | 4 | 4 |
| E | 2% HIGH M | 1.25 mg/ml CaSO4 | 2 | 4 |
| F | 2% HIGH M | 0.63 mg/ml CaSO4 | 1 | 3 |

| DAY 1 | ALGINATE | GELLING | Aggs SETTING | Aggs CLUMPING |
|---|---|---|---|---|
| A | 2% HIGH G | 2.5 mg/ml CaSO4 | 0% | 10% |
| B | 2% HIGH G | 1.25 mg/ml CaSO4 | 20% | 30% |
| CONTROL 1 | 2% HIGH G | 0 | 0% | 0% |
| D | 2% HIGH M | 2.5 mg/ml CaSO4 | 0% | 10% |
| E | 2% HIGH M | 1.25 mg/ml CaSO4 | 10% | 20% |
| CONTROL 2 | 2% HIGH M | 0 | 50% | 10% |

READY-TO-PRINT CELLS AND INTEGRATED DEVICES

CROSS-REFERENCE TO RELATED APPLICATIONS

This application claims benefit of U.S. Provisional Application No. 61/992,184, filed May 12, 2014, which is hereby incorporated herein by reference in its entirety.

BACKGROUND

Regenerative medicine is showing great promise in the clinic, but the cost and availability of the cellular materials from which researchers can perform experiments and clinical trials is holding the field back. There is a strong need for standardized primary cells manufactured at high quality and low cost, and delivered to translational researchers and device manufactures in quantities and formats that accelerate product development and manufacturing efforts. There is also a need for cellular formats that have sufficient shelf life for tissue engineering applications, such as bioprinting. In particular, mesenchymal stem cell (MSC) in a ready-to-use and stable format are needed for tissue engineering and cell therapy applications.

SUMMARY

Disclosed herein are compositions, devices, and methods that provide cellular materials in "ready to use" formats for experimental, therapeutic, and tissue engineering protocols. For example, compositions containing frozen or non-frozen cell present as aggregates are disclosed, including aggregates that comprise mesenchymal stem cells. The aggregates can contain on average about 100 to 200,000 cells per aggregate, including about 1,000 to about 100,000 cells per aggregate. In some cases, the aggregates contain on average about 1,000, 5,000, 10,000, 20,000, 30,000, 40,000, 50,000, 60,000, 70,000, 80,000, 90,000, 100,000, 110,000, 120,000, 130,000, 140,000, 150,000, 160,000, 170,000, 180,000, 190,000, or 200,000 cells per aggregate. As an example, cell aggregates can be used as building blocks for tissue engineering, e.g., by 3D printing, as well as for functional implantable objects for cell therapy applications. Therefore, a hallmark of cell aggregates is the ability of the individual cells within the aggregates to maintain their viability and functions, and when aggregates fuse with each other in culture they are able to form functional tissue. Thus, the ability of aggregates to fuse can demonstrate good cell viability and function. Aggregates are also preferably of similar size and volume. For example, in some embodiments, each of the cell aggregates within the composition have a mean diameter variance less than 5%, 6%, 7%, 8%, 9%, 10%, 11%, 12%, 13%, 14%, 15%, 16%, 17%, 18%, 19%, 20%.

The disclosed compositions can further comprise a cryopreservative and/or biopreservative agent in an amount sufficient to maintain a cell viability of at least 70%. For example, the cells can be frozen cells with an amount of cryopreservative agent, such as Dimethyl sulfoxide (DMSO), sufficient to retain the ability of the cell aggregates to fuse after being stored for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 months at −10 to −80° C., such as −20° C. As another example, the cells can be non-frozen cells with an amount of biopreservative agent, such as HypoThermosol®, sufficient to retain the ability of the cell aggregates to fuse after being stored for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days at 0 to 25° C., such as 4° C.

The cells of the disclosed compositions can be any cells capable of forming cell aggregates and fusing when cultured together. In some cases, the cells are undifferentiated stem cells or progenitor cells with a cell lineage potential that corresponds to the desired tissue being engineered. The cells can be unipotent, oligopotent, multipotent, or pluripotent. In some embodiments, the cells are adult stem cells. The cells are preferably allogeneic or autologous. In particular embodiments, the cells include mesenchymal stem cells (MSCs). The composition can contain a single cell type, such as MSCs. However, in some embodiments, the composition contains two or more different types of cells, i.e., cells of two or more different lineages. The cells can be animal cells, such as human cells.

Also disclosed a compositions containing cellular materials that after storage are suitable for dispersion, e.g. by 3D printing. The disclosed composition contains cells suspended in a viscous matrix such that the cells are at an average cell density of from 1 to 100 million cells per milliliter, including 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 million cells per milliliter. In addition, the viscous matrix can have a viscosity effective to maintain a cell density variance in the composition less than 5%, 6%, 7%, 8%, 9%, 10%, 11%, 12%, 13%, 14%, 15%, 16%, 17%, 18%, 19%, 20% for at least 24, 36, 48, 72, or 120 hours. In some embodiments, the cells in the composition have a cell viability of at least 70% after being stored for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days at 0 to 25° C., such as 4° C. By "viability" is meant that the cells are alive and functional. Functions of a cell can vary depending on the type of cell, but include the ability to replicate, secrete cytokines, secrete growth factors, adhere to tissue culture plastic, adhere to other cells, migrate, or any combination thereof. In some cases, determining viability involves the detecting the presence and/or activity of one or more enzymes produced by the cell. As above, the cells can be present as aggregates. One important way to evaluate the viability of cells in an aggregate is to test the ability of the aggregates to fuse. Therefore, the composition can further comprises a biopreservative agent, a cryopreservative agent, or a combination thereof.

The viscous matrix used to suspend the cells can be any biocompatible polymer suitable for 3D printing and/or tissue engineering. In some cases, the polymer is a biopolymer. For example, suitable biopolymers include polysaccharides, polypeptides, and glycoproteins. This includes natural or synthetically-derived extracellular matrix (ECM) molecules. In some embodiments, the biocompatible polymer comprises alginate. The viscosity of the biocompatible polymer can be adjusted to maintain suspension of the cells while also preferably being fluid enough for dispersion, e.g., by injection through a needle or nozzle. In particular embodiments, the cells maintain a density variance in the composition less than 5%, 10%, 15%, or 20% for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days.

Also disclosed is a kit for producing bioink compositions. In some cases, the kit contains a composition comprising cell aggregates containing on average about 1,000 to about 100,000 cells per aggregate. The kit can also contain a biocompatible polymer. The biocompatible polymer can be in the same or different container as the cell aggregates. The kit can also contain a crosslinking agent. This agent can also be in the same or different container as the cell aggregates, so long as the biocompatible polymer and crosslinking agent are in different containers.

Also disclosed is a closed system device comprising a cell material composition described herein. The closed system device can be configured to dispense the composition on a surface as a discrete unit. For example, each discrete unit can in some embodiments contains a controlled amount of the cells. An example of a closed system device is a cartridge, such as a cartridge for use in a three-dimensional (3D) printer device.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
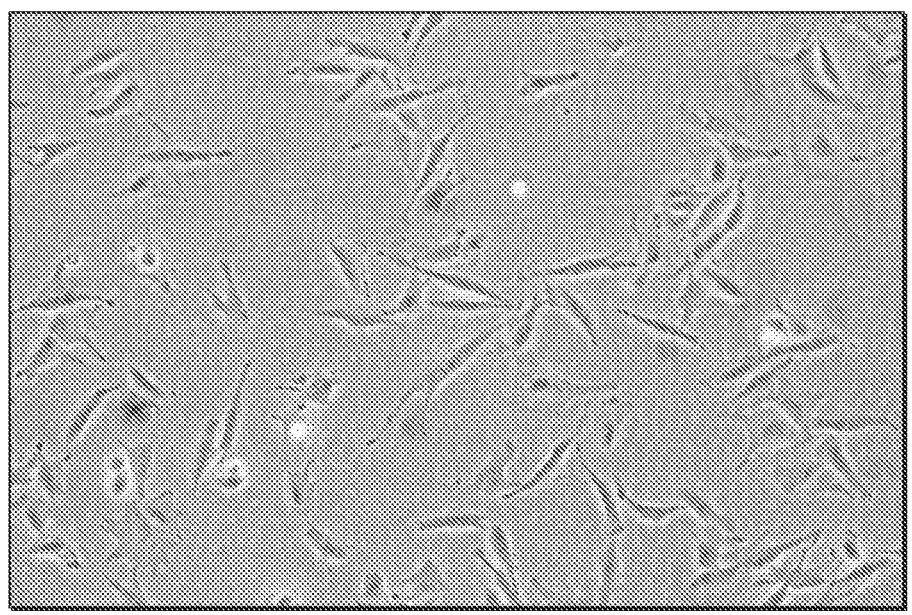
FIG. 1A shows image of mesenchymal stem cells (MSCs) adhering 2 hr after plating.

The disclosed compositions, devices, and methods relate to the fields of regenerative medicine, stem cell-based technologies and medical devices, tissue engineering, biomedical research and development, cellular raw materials and biofunctional materials derived from living cells. Particularly, stable compositions and formulations of functional living cells that are delivered in formats that enable the incorporation of these cells or cell-derived materials into biological and biomedical products are disclosed.

Provided herein are stable formulations of highly functional living cells that enable the incorporation of cells into engineered tissues, medical devices, or other products that require functional living cells. For example, cell compositions for use in regenerative medicine, tissue engineering, and bioprinting applications are disclosed. The stable formulations provided herein maintain the cells or cellular aggregates in suspension in a state of high viability and functionality The compositions can contain formulations of cells as single cell suspensions or as homogeneous or heterogeneous cell aggregated cells that are ready to use after several days, weeks, or months of storage. The cell formulations allow for maintained cell viability and functionality. The cells in some of the formulations preferably remain in suspension without settling during storage and have the ability to be delivered to a specific location while maintaining viability and function.

The stable formulations can be stable for weeks to months or years, either in a frozen (i.e. cryopreserved) or a non-frozen (biopreserved) state. By frozen state, it is meant that the stable formulations are at or below a freezing temperature (e.g., at or below 0 degrees Celsius, and typically at least −20 degrees Celsius). In some embodiments, formulations stored in a frozen state further comprise a cryopreservative agent. By a non-frozen state, it is meant that the stable formulations are above a freezing temperature (e.g., at or above 0 degrees Celsius), typically at least 2 degrees Celsius. In some embodiments, the non-frozen state includes 0 to 37 degrees Celsius, such as 4 to 24 degrees Celsius.

The term "cell" as used herein also refers to individual cells, cell lines, primary culture, or cultures derived from such cells unless specifically indicated. A "culture" refers to a composition comprising isolated cells of the same or a different type.

In some embodiments, the disclosed composition contains stem cells or progenitor cells. Pluripotential stem cells, adult stem cells, blastocyst-derived stem cells, gonadal ridge-derived stem cells, teratoma-derived stem cells, totipotent stem cells, multipotent stem cells, oncostatin-independent stem cell (OISCs), embryonic stem cells (ES), embryonic germ cells (EG), and embryonic carcinoma cells (EC) are all examples of stem cells. Stem cells can have a variety of different properties and categories of these properties. For example in some forms stem cells are capable of proliferating for at least 10, 15, 20, 30, or more passages in an undifferentiated state. In some forms the stem cells can proliferate for more than a year without differentiating. Stem cells can also maintain a normal karyotype while proliferating and/or differentiating. Stem cells can also be capable of retaining the ability to differentiate into mesoderm, endoderm, and ectoderm tissue, including germ cells, eggs and sperm. Some stem cells can also be cells capable of indefinite proliferation in vitro in an undifferentiated state. Some stem cells can also maintain a normal karyotype through prolonged culture. Some stem cells can maintain the potential to differentiate to derivatives of all three embryonic germ layers (endoderm, mesoderm, and ectoderm) even after prolonged culture. Some stem cells can form any cell type in the organism. Some stem cells can form embryoid bodies under certain conditions, such as growth on media which do not maintain undifferentiated growth. Some stem cells can form chimeras through fusion with a blastocyst, for example.

Some stem cells can be defined by a variety of markers. For example, some stem cells express alkaline phosphatase. Some stem cells express SSEA-1, SSEA-3, SSEA-4, TRA-1-60, and/or TRA-1-81. Some stem cells do not express SSEA-1, SSEA-3, SSEA-4, TRA-1-60, and/or TRA-1-81. Some stem cells express Oct 4, Sox2, and Nanog. It is understood that some stem cells will express these at the mRNA level, and still others will also express them at the protein level, on for example, the cell surface or within the cell.

In some embodiments, the disclosed composition comprises a cell other than a stem cell. The adult human body produces many different cell types. These different cell types include, but are not limited to, Keratinizing Epithelial Cells, Wet Stratified Barrier Epithelial Cells, Exocrine Secretory Epithelial Cells, Hormone Secreting Cells, Epithelial Absorptive Cells (Gut, Exocrine Glands and Urogenital Tract), Metabolism and Storage cells, Barrier Function Cells (Lung, Gut, Exocrine Glands and Urogenital Tract), Epithelial Cells Lining Closed Internal Body Cavities, Ciliated Cells with Propulsive Function, Extracellular Matrix Secretion Cells, Contractile Cells, Blood and Immune System Cells, Sensory Transducer Cells, Autonomic Neuron Cells, Sense Organ and Peripheral Neuron Supporting Cells, Central Nervous System Neurons and Glial Cells, Lens Cells, Pigment Cells, Germ Cells, and Nurse Cells.

Cells of the human body include Keratinizing Epithelial Cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet Stratified Barrier Epithelial Cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining bladder and urinary ducts), Exocrine Secretory Epithelial Cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (HCl secretion), Pancreatic acinar cell (bicarbonate and digestive enzyme secretion), Paneth cell of small intestine (lysozyme secretion), Type II pneumocyte of lung (surfactant secretion), Clara cell of lung, Hormone Secreting Cells, Anterior pituitary cell secreting growth hormone, Anterior pituitary cell secreting follicle-stimulating hormone, Anterior pituitary cell secreting luteinizing hormone, Anterior pituitary cell secreting prolactin, Anterior pituitary cell secreting adrenocorticotropic hormone, Anterior pituitary cell secreting thyroid-stimulating hormone, Intermediate pituitary cell secreting melanocyte-stimulating hormone, Posterior pituitary cell secreting oxytocin, Posterior pituitary cell secreting vasopressin, Gut and respiratory tract cell secreting serotonin, Gut and respiratory tract cell secreting endorphin, Gut and respiratory tract cell secreting somatostatin, Gut and respiratory tract cell secreting gastrin, Gut and respiratory tract cell secreting secretin, Gut and respiratory tract cell secreting cholecystokinin, Gut and respiratory tract cell secreting insulin, Gut and respiratory tract cell secreting glucagon, Gut and respiratory tract cell secreting bombesin, Thyroid gland cell secreting thyroid hormone, Thyroid gland cell secreting calcitonin, Parathyroid gland cell secreting parathyroid hormone, Parathyroid gland oxyphil cell, Adrenal gland cell secreting epinephrine, Adrenal gland cell secreting norepinephrine, Adrenal gland cell secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Kidney juxtaglomerular apparatus cell (renin secretion), Macula densa cell of kidney, Peripolar cell of kidney, Mesangial cell of kidney, Epithelial Absorptive Cells (Gut, Exocrine Glands and Urogenital Tract), Intestinal brush border cell (with microvilli), Exocrine gland striated duct cell, Gall bladder epithelial cell, Kidney proximal tubule brush border cell, Kidney distal tubule cell, Ductulus efferens nonciliated cell, Epididymal principal cell, Epididymal basal cell, Metabolism and Storage Cells, Hepatocyte (liver cell), White fat cell, Brown fat cell, Liver lipocyte, Barrier Function Cells (Lung, Gut, Exocrine Glands and Urogenital Tract), Type I pneumocyte (lining air space of lung), Pancreatic duct cell (centroacinar cell), Nonstriated duct cell (of sweat gland, salivary gland, mammary gland, etc.), Kidney glomerulus parietal cell, Kidney glomerulus podocyte, Loop of Henle thin segment cell (in kidney), Kidney collecting duct cell, Duct cell (of seminal vesicle, prostate gland, etc.), Epithelial Cells Lining Closed Internal Body Cavities, Blood vessel and lymphatic vascular endothelial fenestrated cell, Blood vessel and lymphatic vascular endothelial continuous cell, Blood vessel and lymphatic vascular endothelial splenic cell, Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye, Corneal endothelial cell, Ciliated Cells with Propulsive Function, Respiratory tract ciliated cell, Oviduct ciliated cell (in female), Uterine endometrial ciliated cell (in female), Rete testis cilated cell (in male), Ductulus efferens ciliated cell (in male), Ciliated ependymal cell of central nervous system (lining brain cavities), Extracellular Matrix Secretion Cells, Ameloblast epithelial cell (tooth enamel secretion), Planum semilunatum epithelial cell of vestibular apparatus of ear (proteoglycan secretion), Organ of *Corti* interdental epithelial cell (secreting tectorial membrane covering hair cells), Loose connective tissue fibroblasts, Corneal fibroblasts, Tendon fibroblasts, Bone marrow reticular tissue fibroblasts, Other (nonepithelial) fibroblasts, Blood capillary pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Contractile Cells, Red skeletal muscle cell (slow), White skeletal muscle cell (fast), Intermediate skeletal muscle cell, Muscle spindle—nuclear bag cell, Muscle spindle—nuclear chain cell, Satellite cell (stem cell), Ordinary heart muscle cell, Nodal heart muscle cell, Purkinje fiber cell, Smooth muscle cell (various types), Myoepithelial cell of iris, Myoepithelial cell of exocrine glands, Blood and Immune System Cells, Erythrocyte (red blood cell), Megakaryocyte, Monocyte, Connective tissue macrophage (various types), Epidermal Langerhans cell, Osteoclast (in bone), Dendritic cell (in lymphoid tissues), Microglial cell (in central nervous system), Neutrophil, Eosinophil, Basophil, Mast cell, Helper T lymphocyte cell, Suppressor T lymphocyte cell, Killer T lymphocyte cell, IgM B lymphocyte cell, IgG B lymphocyte cell, IgA B lymphocyte cell, IgE B lymphocyte cell, Killer cell, Stem cells and committed progenitors for the blood and immune system (various types), Sensory Transducer Cells, Photoreceptor rod cell of eye, Photoreceptor blue-sensitive cone cell of eye, Photoreceptor green-sensitive cone cell of eye, Photoreceptor red-sensitive cone cell of eye, Auditory inner hair cell of organ of *Corti*, Auditory outer hair cell of organ of *Corti*, Type I hair cell of vestibular apparatus of ear (acceleration and gravity), Type II hair cell of vestibular apparatus of ear (acceleration and gravity), Type I taste bud cell, Olfactory neuron, Basal cell of olfactory epithelium (stem cell for olfactory neurons), Type I carotid body cell (blood pH sensor), Type II carotid body cell (blood pH sensor), Merkel cell of epidermis (touch sensor), Touch-sensitive primary sensory neurons (various types), Cold-sensitive primary sensory neurons, Heat-sensitive primary sensory neurons, Pain-sensitive primary sensory neurons (various types), Proprioceptive primary sensory neurons (various types), Autonomic Neuron Cells, Cholinergic neural cell (various types), Adrenergic neural cell (various types), Peptidergic neural cell (various types), Sense Organ and Peripheral Neuron Supporting Cells, Inner pillar cell of organ of *Corti*, Outer pillar cell of organ of *Corti*, Inner phalangeal cell of organ of *Corti*, Outer phalangeal cell of organ of *Corti*, Border cell of organ of *Corti*, Hensen cell of organ of *Corti*, Vestibular apparatus supporting cell, Type I taste bud supporting cell, Olfactory epithelium supporting cell, Schwann cell, Satellite cell (encapsulating peripheral nerve cell bodies), Enteric glial cell, Central Nervous System Neurons and Glial Cells, Neuron cell (large variety of types, still poorly classified), Astrocyte glial cell (various types), Oligodendrocyte glial cell, Lens Cells, Anterior lens epithelial cell, Crystallin-containing lens fiber cell, Pigment Cells, Melanocyte, Retinal pigmented epithelial cell, Germ Cells, Oogonium/oocyte, Spermatocyte, Spermatogonium cell (stem cell for spermatocyte), Nurse Cells, Ovarian follicle cell, Sertoli cell (in testis), and Thymus epithelial cell.

In some cases, the cells are mesenchymal stem cells (MSCs) or bone marrow stromal cells (BMSCs). These terms are used synonymously throughout herein. MSCs are of interest because they are easily isolated from a small aspirate of bone marrow, or other mesenchymal stem cell sources, and they readily generate single-cell derived colonies. Bone marrow cells may be obtained from iliac crest, femora, tibiae, spine, rib, knee or other mesenchymal tissues. Other sources of MSCs include embryonic yolk sac, placenta, umbilical cord, skin, fat, synovial tissue from joints, and blood. The presence of MSCs in culture colonies may be verified by specific cell surface markers which are identified with monoclonal antibodies. See U.S. Pat. Nos. 5,486,359 and 7,153,500. The single-cell derived colonies can be expanded through as many as 50 population doublings in about 10 weeks, and can differentiate into osteoblasts, adipocytes, chondrocytes (Friedenstein et al., 1970 Cell Tissue Kinet. 3:393-403; Castro-Malaspina, et al., 1980 Blood 56:289-301; Beresford et al., 1992 J. Cell Sci. 102: 341-351; Prockop, 1997 Science 276:71-74), myocytes (Wakitani et al, 1995 Muscle Nerve 18:1417-1426), astrocytes, oligodendrocytes, and neurons (Azizi et al., 1998 Proc. Natl. Acad. Sci. USA 95:3908-3913); Kopen et al 1999 Proc. Natl. Acad. Sci. USA 96:10711-10716; Chopp et al., 2000 Neuroreport II 3001-3005; Woodbury et al., 2000 Neuroscience Res. 61:364-370). In rare instances, the cells can differentiate into cells of all three germlines Thus, MSCs serve as progenitors for multiple mesenchymal cell lineages including bone, cartilage, ligament, tendon, adipose, muscle, cardiac tissue, stroma, dermis, and other connective tissues. See U.S. Pat. Nos. 6,387,369 and 7,101,704. For these reasons, MSCs currently are being tested for their potential use in cell and gene therapy of a number of human diseases (Horwitz et al., 1999 Nat. Med. 5:309-313; Caplan, et al. 2000 Clin. Orthoped. 379:567-570).

Methods for creating MSC aggregates are described in US 2012/0219572 by Prockop et al, and Bartosh, et al. PNAS 2010 107(31):13724-13729, which are incorporated by reference in their entirety for this teaching. For example, MSCs can be cultured in a manner that promotes aggregation and formation of spheroids. For example, MSCs can be isolated from human bone marrow and cultured in complete medium (DMEM low glucose containing 4 mM L-glutamine, 10% PBS, and 1% penicillin/streptomycin) in hanging drops or on non-adherent dishes. Any medium capable of supporting MSCs in vitro may be used to culture the MSCs. Media formulations that can support the growth of MSCs include, but are not limited to, Dulbecco's Modified Eagle's Medium (DMEM), alpha modified Minimal Essential Medium (aMEM), and Roswell Park Memorial Institute Media 1640 (RPMI Media 1640) and the like. Typically, up to 20% fetal bovine serum (FBS) or 1-20% horse serum is added to the above medium in order to support the growth of MSCs. A defined medium, however, can also be used if the growth factors, cytokines, and hormones necessary for culturing MSCs are provided at appropriate concentrations in the medium. Media useful in the disclosed methods of may contain one or more compounds of interest, including but not limited to antibiotics, mitogenic or differentiation compounds useful for the culturing of MSCs. The cells may be grown, for example, at temperatures from 27° C. to 40° C., including from 31° C. to 37° C. The carbon dioxide content may be maintained between 2% to 10% and the oxygen content may be maintained between 1% and 22%.

In some embodiments, the MSCs are cultured under conditions and for a period of time sufficient to provide a sufficient number of cells for further culturing. The cells are then cultured under conditions which promote the formation of spheroidal aggregates of the cells. In some embodiments, the cells are cultured in Aggrewell™ plates. In some embodiments, the cells are cultured as hanging drops. In some embodiments, each hanging drop of MSCs that is cultured contains from about 1,000 to about 500,000 cells/drop. The hanging drops of MSCs can then be cultured for a period of time sufficient for forming spheroidal aggregates of the mesenchymal stem cells. In general, the drops of cells are cultured for a period of time of up to 4 days.

The cells can be derived from a human or other animal. For example, cells can originate from a mouse, guinea pig, rat, cattle, horses, pigs, sheep, or goat. In some embodiments, the cells originate from non-human primates. In some cases, the cells are autologous or allogenic.

In some cases, the cells are obtained from a cell culture, which involves population doubling (cell passages). In these cases, the cells are preferably from a population doubling less than or equal to 50, including a population doubling between 4 and 50, between 10 and 30. Therefore the cells can be from passage number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

There are several biomaterials that can be used in tissue engineering and cell delivery, with most of these materials being considered "hydrogels", or water-containing gels. The requirements for these materials are 1) biocompatibility: cells must be able to be combined with the materials, often throughout the material, and remain viable and functional, and 2) in most cased the hydrogels must also facilitate migration, proliferation and differentiation of the embedded and endogenous, cells. There are additional constraints for maintaining "printability" of hydrogels, while still keeping initial requirements of biocompatibility and migration/function. These are outlined in the review by Malda, J, et al, Adv. Mater. 2013, 25, 5011-5028. In addition, many commercial sources of hydrogels that can be used for bio-printing are described by Murphy S V, Skardal A, Atala A. 2013. Evaluation of hydrogels for bio-printing applications. J Biomed Mater Res Part A 2013:101A:272-284, including Collagen Type I, Collagen/Fibrin, Fibrin, Extracel™ hydrogel, Extracel™ UV, Tyramine substituted hyaluronic acid (TS-NaHy), Corgel™, Methylcellulose-Hyaluronan (MC-HA), Chitosan, Chitosan/Collagen, Alginate, Alginate/Gelatin, and Polyethylene Glycol Diacrylate (PEGDA).

Common materials used in tissue engineering and bio-printing are alginates, collagens, fibrins, fibrinogens, polyethylene glycols (PEGs), agar, agarose, chitosan, hyaluronan, methacrylamide, gelatins, pluronics, matrigel, methylcellulose, and PEG-DA (diacrylate). These materials are often not used simply alone, but are often mixed together to combine properties (e.g. gelling properties of alginates or PEG-DA with cell adhesion abilities of collagens/fibrins) to make new compositions. Furthermore, new hydrogels can be designed from the ground up to account for these properties (Guvendiren and Burdick, Current Opinion in Biotechnology 2013, 24:841-846).

Hydrogels for use in the disclosed compositions and methods are compatible with dispensing/printing of cells while also having the ability of having cells remain viable and functional for several days/weeks/months during the biopreservation process.

The compositions provided herein comprise cells that maintain high viability and functionality after extended storage. By viability it is meant that after preservation or storage, the cells are alive and capable of the same cell functions in existence prior to storage. In some cases, high viability means that at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% of the initial cell population is capable of survival, growth, and function after preservation or storage.

Cell viability can be determined using methods known in the art. A viability assay is an assay to determine the ability of organs, cells or tissues to maintain or recover viability. Viability can be distinguished from the all-or-nothing states of life and death by use of a quantifiable index between 0 and 1 (or 0 and 100%) (Pegg D E (1989). "Viability assays for preserved cells, tissues, and organs". Cryobiology 26(3): 212-231). For example, examining the ratio of potassium to sodium in cells can serve as an index of viability. If the cells do not have high intracellular potassium and low intracellular sodium, then the cell membrane may not be intact, and/or (2) the sodium-potassium pump may not be operating well. Thus, many assays that measure cell membrane integrity are used as quantitatie measures of viability. These can be Trypan Blue, propidium iodide (PI), which are dyes that can penetrate leaky cell membranes and have been automated in commercially available cell counters. Other types of assays measure the overall metabolic rate of cell populations such as measuring total ATP, formazan-based assays (MTT/XTT) and Alomar blue-based or Resazurin-based assays. However quantitative measures of physiological function do not indicate whether damage repair and recovery is possible. An assay of the ability of a cell to adhere to a surface, spread and eventually migrate and divide may be more indicative of a live cell, but can make considerable more time and can be less quantitative. With that said, all of these tests can be used as viability assays to assess the success of cryopreservation techniques, the toxicity of substances, or the effectiveness of substances in mitigating effects of toxic substances.

In the disclosed studies, an automated PI membrane integrity assay (NucleoCounter® NC100 by Chemometech® Inc), was used as a fluorescent Live/Dead assay, and Alomar Blue was used to measure cell metabolism of aggregates. Functional tests were also used that show that the cells within aggregates can still adhere to cell culture plastic and grow out from the aggregate, and when the aggregates are maintained on non-adhesive surfaces the cells at the aggregate edge will join with other aggregates, creating fusion of aggregates into single, larger structures. It is the general assumption that many of the cell functions such as cytokine secretion, differentiation, and immunomodulatory function of hMSCs are maintained if the cells are still capable of adhering and spreading on culture plates, or if the cellular aggregates fuse (which is the 3D equivalent of adhering and spreading)

High viability of the cells (e.g., MSCs) in the compositions can be maintained as a result of the aqueous solutions in which the cells are stored. The aqueous solutions can, for example, comprise chemicals and nutrients that reduce cellular apoptosis and cellular death.

Therefore, in some embodiments, the compositions contain a cryopreservative agent. Non limiting examples of cryopreservative agents include dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, inorganic salts, or any combination thereof. In some cases, the cryopreservative contains CryoStor® CS2, CS5, or CS10 freeze media (BioLife Solutions®, Inc) and 5% DMSO. In some cases, the cryopreservative contains between 1% and 15% DMSO, such as 2% to 7.5%, including 5% DMSO.

In some embodiments, the disclosed cell composition comprises a biopreservative agent that scavenges free radicals, provides pH buffering, provides oncotic/osmotic support, contains energy substrates, has ionic concentrations that balance the intracellular state at low temperatures, or any combination thereof. For example, in some embodiments, the biopreservation formulation comprises Hypo-Thermosol® (BioLife Solutions®, Inc.), such as Hypo-Thermosol®FRS. The components of HypoThermosol® FRS include Trolox (6-hydroxy-2,5,7,8-tetramethylchroman-2-carboxylic acid), $Na^+$, $K^+$, $Ca^{2+}$, $Mg^{2+}$, $Cl^-$, $H_2PO4^-$, $HCO3^-$, HEPES, Lactobionate, Sucrose, Mannitol, Glucose, Dextran-40, Adenosine, and Glutathione, with a pH 7.6, and an osmolality of about 360. Therefore, in some embodiments, the disclosed cell composition comprises 2-10% DMSO and HypoThermosol® or HypoThermosol®FRS.

The compositions provided herein comprise cells at high volumes and high cell concentrations. In some embodiments, the disclosed cell compositions contain at least 10 million cells at a concentration of at least 1 million cells/mL. For example, in some embodiments, the composition comprises at least 10 million, 100 million, 1 billion, 10 billion, or 50 billion cells at a concentration of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 million cells/mL.

In some embodiments, the disclosed cells are present as multicellular aggregates that act as "micro-tissues", and can be used for building blocks for higher ordered 3D tissues when printed, or stable formats for transplanted cells in cell therapy applications. These aggregates therefore preferably have a uniform size and shape, although heterogeneous sized and shaped multicellular aggregates can be sufficient in many applications. The aggregates are also preferably dispersed within the cell composition uniformly so as to provide consistent numbers of cells when dispensed, extruded, or printed.

The size and density of the aggregates can be selected based on the intended use. In some embodiments, the cells are present in aggregates containing at least 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, or 200,000 cells per aggregate. The aggregates preferably have a diameter variance less than 5%, 6%, 7%, 8%, 9%, 10%, 15%, or 20% within each composition.

In some embodiments, the disclosed cells are suspended in a viscous solution (i.e., extrusion material) that maintains the cells in suspension to enhance uniform distribution within the composition, while also maintaining suitability of the composition for extrusion, e.g., for bioprinting. By "uniform distribution" is meant that the cells have a density variance less than 5%, 6%, 7%, 8%, 9%, 10%, 15% or 20% within each composition. For example, the viscous solution can be a hydrogel, such as those described above. The viscosity is therefore preferably high enough to maintain uniform distribution while low enough to be suitable for extrusion by a bioprinter.

In some embodiments, the disclosed compositions (bioinks) are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. Viscosity can be measured by routine methods with a viscometer.

In some cases, the extrusion material is also a biomaterial suitable for tissue engineering, such as collagen, hyaluronate, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide), poly(ethylene glycol), and copolymers thereof, poly(vinyl alcohol), polyphosphazene, and combinations thereof.

In some embodiments, an extrusion compound comprises a photoinitiator, which is a molecule that upon absorption of light at a specific wavelength produces reactive species capable of catalyzing polymerization or polycondensation reactions. These reactions area also called photopolymerization or radiation curing. Photoinitiators are typically ketones which contain both aromatic and carbonyl groups.

In some embodiments, hydrogel-based extrusion compounds are thermoreversible gels (also known as thermoresponsive gels or thermogels). In some embodiments, a suitable thermoreversible hydrogel is not a liquid at room temperature. Polymers composed of polyoxypropylene and polyoxyethylene form thermoreversible gels when incorporated into aqueous solutions. These polymers have the ability to change from the liquid state to the gel state at temperatures that can be maintained in a bioprinter apparatus. The liquid state-to-gel state phase transition is dependent on the polymer concentration and the ingredients in the solution.

The stable cell formulations can be stored, for example, in a traditional screw or septum top bottle, or within a sterile closed-system device that can be removed from frozen- or non-frozen-storage and integrated with a dispensing device. The dispensing device can, for example, be a bioprinter or an automated or automated or manual injection device. Optionally, the bioprinter can be a three dimensional (3D) bioprinter. The dispensing device can deliver the living cells to specific locations while maintaining the sterility and quality of cells. Therefore, in some embodiments, the disclosed cell compositions are contained within a sterile or aseptic bioink cartridge or biomedical syringe.

In some embodiments, the disclosed homogenous cell population and a viscous solution comprises a bio-ink for use in bioprinting. As used herein, "bio-ink" means a liquid, semi-solid, or solid composition comprising a plurality of cells. In some embodiments, bio-ink comprises cell suspensions, cell aggregates, cell-comprising gels, multicellular bodies, or tissues. In some embodiments, the bio-ink additionally comprises support material. In some embodiments, the bio-ink additionally comprises non-cellular materials that provide specific biomechanical properties that enable bioprinting.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated, computer-aided, three-dimensional prototyping device (e.g., a bioprinter).

As used herein, "cartridge" means any object that is capable of receiving (and holding) a bio-ink or a support material.

In some embodiments, the container or cartridge has sterile ports or tubing that allows the cells and biomaterials to be expelled from the container or cartridge while maintain aseptic conditions where necessary.

In some embodiments, a bioprinter dispenses bio-ink from the cartridge in a specific pattern and at specific positions as directed by a computer aided design software in order to form a specific cellular construct, tissue, or organ. In order to fabricate complex tissue constructs, the bioprinter deposits the bio-ink at precise speeds and in uniform amounts. In some embodiments, a cartridge comprises one dispensing orifice. In various other embodiments, a cartridge comprises 2, 3, 4, 5, 6, 7, 8, 9, 10, 11, 12, 13, 14, 15, 20, 30, 40, 50, 60, 70, 80, 90, 100, or more dispensing orifices. In further embodiment, the edges of a dispensing orifice are smooth or substantially smooth.

Many types of cartridges are suitable for use with bioprinters. In some embodiments, a cartridge is compatible with bioprinting that involves extruding a semi-solid or solid bio-ink or a support material through one or more dispensing orifices. In some embodiments, a cartridge is compatible with bioprinting that involves dispensing a liquid or semi-solid cell solution, cell suspension, or cell concentration through one or more dispensing orifices. In some embodiments, a cartridge is compatible with non-continuous bioprinting. In some embodiments, a cartridge is compatible with continuous and/or substantially continuous bioprinting.

In some embodiments, a cartridge is a capillary tube or a micropipette. In some embodiments, a cartridge is a syringe or a needle. Many internal diameters are suitable for substantially round or cylindrical cartridges. In various embodiments, suitable internal diameters include, by way of non-limiting examples, 1, 10, 50, 100, 200, 300, 400, 500, 600, 700, 800, 900, 1000 or more µm, including increments therein. In other various embodiments, suitable internal diameters include, by way of non-limiting examples, 1, 2, 3, 4, 5, 6, 7, 8, 9, 10, 20, 30, 40, 50, 60, 70, 80, 90, 100 or more mm, including increments therein. In some embodiments, a cartridge has an internal diameter of about 1 µm to about 1000 µm. In a particular embodiment, a cartridge has an internal diameter of about 500 µm. In another particular embodiment, a cartridge has an internal diameter of about 250 µm. Many internal volumes are suitable for the cartridges disclosed herein. In various embodiments, suitable internal volumes include, by way of non-limiting examples, 0.1, 1, 10, 20, 30, 40, 50, 100, 200, 300, 400, 500, 600, 700, 800, 900, 1000 or more ml, including increments therein. In other various embodiments, suitable internal volumes include, by way of non-limiting examples, 1, 2, 3, 4, 5, 10, 20, 30, 40, 50, 60, 70, 80, 90, 100, 199, 300, 400, 500 or more ml, including increments therein.

In some embodiments, a cartridge is compatible with ink-jet printing of bio-ink and/or support material onto a receiving 2D or 3D surface such as that described in U.S. Pat. No. 7,051,654. In further embodiments, a cartridge includes dispensing orifices in the form of voltage-gated nozzles or needles under the control of the computer code described herein.

In some embodiments, a cartridge is marked to indicate the composition of its contents. In further embodiments, a cartridge is marked to indicate the composition of a bio-ink contained therein. In some embodiments, the surface of the cartridge is colored. In some embodiments, the outer surface of the cartridge is dyed, painted, marked with a pen, marked by a sticker, or a combination thereof.

In some cases, the cartridge is a single-use manifold system, such as that described in U.S. Pat. No. 6,712,963, which is disclosed herein for the teaching of single-use manifold units. Briefly, disposable tubing and flexible-wall containers can be assembled via aseptic connectors. These manifolds can interact with at least one remotely controlled pinch valve which engages only the outside surface of the manifold tubing. Such manifold and pinch valve systems can be used in conjunction with a peristaltic type of pump, which, together with the remotely operated pinch valve, can be operated by a controller which provides automated and accurate delivery of biotechnology fluid in an aseptic environment while avoiding or reducing cleaning and quality assurance procedures.

The disclosed cartridge is preferably configured to be filled with bioink aseptically and then protect the bioink from exposure to the environment to prevent contamination. Therefore, the cartridge preferably has a seal that maintains the closed system after being filled. The cartridge should also preferably be able to maintain cells in the bioink at a specific temperature. For example, the cartridge can be insulated.

The disclosed cartridge also preferably is configured to eject the bioink within. For example, the bioink can be ejected by air pressure, hydraulic pressure, screw driven pistons, or the like. As ejection can create significant pressures, the cartridge is preferably formed from a rigid material.

The cartridge has at least one orifice for ejection/dispersion of the bioink. However, multiple orifices can speed up printing. In some cases, the 3D printer is configured with two or more cartridges to dispense two or more types of cells. However, in some cases, a single cartridge contains two or more compartments and two or more orifices so as to dispense two types of cells at the same time. Alternatively, 2 or more cell types can be combined in cellular aggregates that are suspended in the biopolymer, or 2 cell types can be mixed together at an optimized ratio within the same hydrogel matrix and extruded at the same time.

In some embodiments, the cartridge contains a composition as disclosed herein containing cells suspended in a viscous matrix such that the cells are viable and ready for printing once removed from storage (e.g., frozen or non-frozen). In some cases, this means that the viscous matrix is sufficiently viscous to keep the cells uniformly dispersed in the composition, i.e., not settled to the bottom of the cartridge.

Also disclosed is a kit for producing bioink compositions. In some cases, the kit contains a composition comprising cell aggregates containing on average at least 100, 110, 120, 130, 140, 150, 160, 170, 180, 190, 200, 210, 220, 230, 240, 250, 260, 270, 280, 290, or 300 up to 200,000 cells per aggregate. The kit can also contain a non-crosslinked biocompatible polymer, such as alginate. The biocompatible polymer can be in the same or different container as the cell aggregates. The kit can also contain a crosslinking agent, such as calcium sulfate. This agent can also be in the same or different container as the cell aggregates, so long as the biocompatible polymer and crosslinking agent are in different containers. The kit can further contain a means for mixing the ingredients of the kit, such as a syringe.

A number of embodiments of the invention have been described. Nevertheless, it will be understood that various modifications may be made without departing from the spirit and scope of the invention. Accordingly, other embodiments are within the scope of the following claims.

EXAMPLES

Figure 1B:
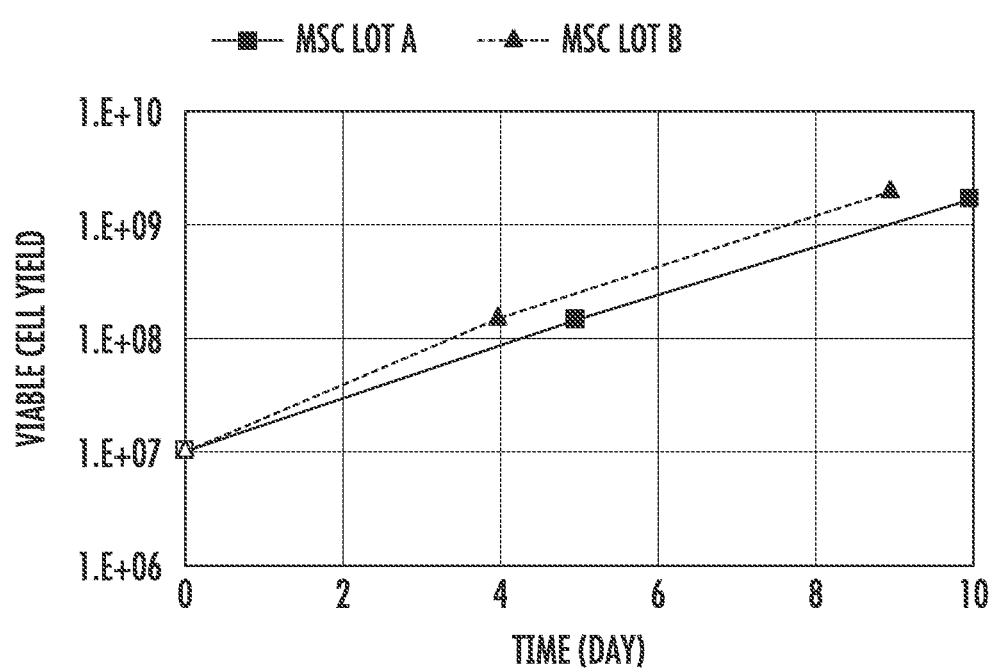
FIG. 1B is a growth curve for two lots of MSCs after being plated and expanded for 2 passages.

Example 1: MSC Characterization hMSCs can be cultured, expanded and cryopreserved. When the cells are thawed they can adhere to plastic, divide and increase in number, and have biological functions relevant to therapy including secreting angiogenic cytokines, and upregulating immunomodulatory enzyme when stimulated with inflammatory molecules like interferon gamma and multipotent trilineage differentiation.

hBM-MSCs are commercially available in a cryopreserved format from several sources. In this experiment, a vial of 10 million hBM-MSCs (vendor, RoosterBio®, Frederick, Md., part # MSC001) are thawed and plated into T225 flasks (Corning) in expansion media (RoosterBio®, part # KT-001). The hMSCs were seeded at 3,000 cells/cm$^2$ and incubated in 37° C. humidified $CO_2$ incubator. Within 2 hours many of the cells were adhering to the culture dish (FIG. 1), which is a prerequisite for cell expansion during culture. The MSCs were culture expanded for 4-5 days before harvesting. Once the cells achieved 80-90% visual cell confluency, they were harvested with TrypLE harvest reagent (Thermo Fisher®) and cell enumeration and viability were 20 quantitated with an automated system called Nucleocounter NC100® (Chemometec®). The cells were also assayed for function. The hMSCs can be serially passaged multiple times, with each passage yielding two to five population doublings depending on media used. The end goal is to achieve cells at a population doubling level high enough so that thousands or tens of thousands of products can be produced from a single donor, and that the biological functions of the cells are maintained.

Figure 2:
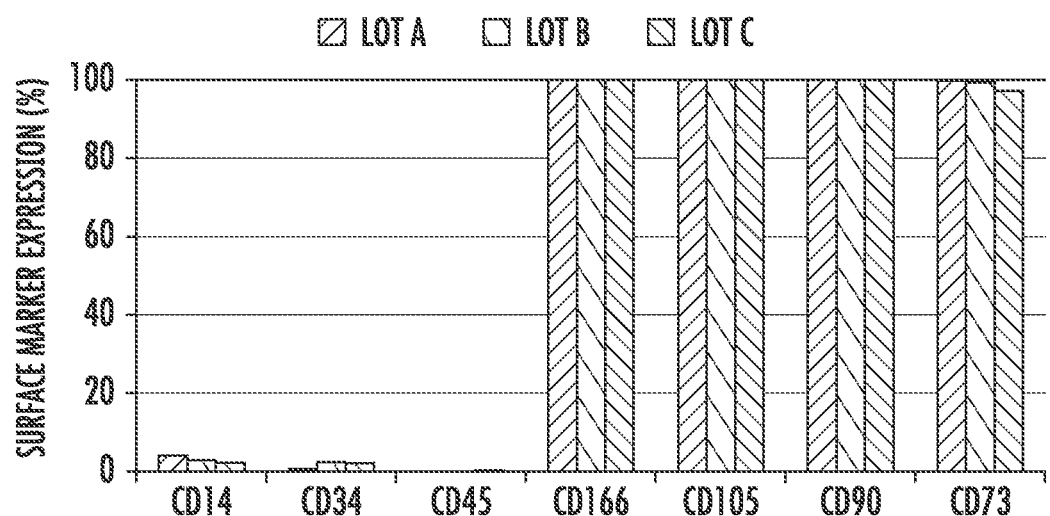
FIG. 2 is a bar graph showing that three lots of MSCs express CD73, CD90, CD105 and CD166, and are negative for CD45, CD34, and CD14, after thawing and expanding the cryopreserved MSC.

MSCs were characterized for standard flow cytometry markers (FIG. 2). The MSCs were cultured for 7-10 days in DMEM+10% serum and assayed by flow cytometry. The cells were positive for CD73, CD90, CD105 and CD166, and negative for CD14, CD34, and CD45.

Figure 3:
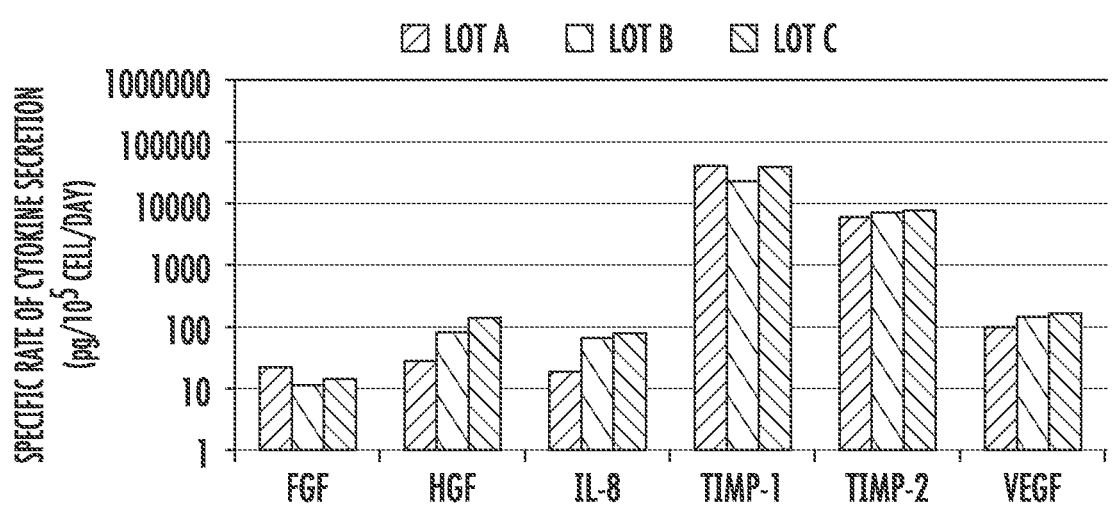
FIG. 3 is a bar graph showing secretion levels of angiogenic cytokine in three lots of MSCs after thawing and expanding the cryopreserved MSC.

Biological Functions: To assay for a panel of biological factors that hMSCs secrete into the culture medium, hMSCs were harvested from culture and plated into 24 well plates at 40,000 cells/cm$^2$ in basal medium (RoosterBio®)+2% bovine serum (Atlas Biologics®). The cells were incubated at 37° C. for 24 hours, +/−1 hour, at which time the cell culture media was collected at frozen at −20° C. The collected media was then assayed using the Q-Plex™ Human Angiogenesis (9-plex, Quansys Biosystmes®) fully quantitative ELISA-based chemiluminescent assay allowing the concurrent measurement of the nine angiogenic biomarkers ANG-2, FGF basic, HGF, IL-8, TIMP-1, TIMP-2, TNFα, VEGF. The multiplexed ELISA provided analytes in pg/mL in the culture supernatant, which was then normalized to the number of cells seeded 5 into the wells and time in culture to obtain a specific cytokine secretion metric in pg/cell/day (FIG. 3).

Figure 4A:
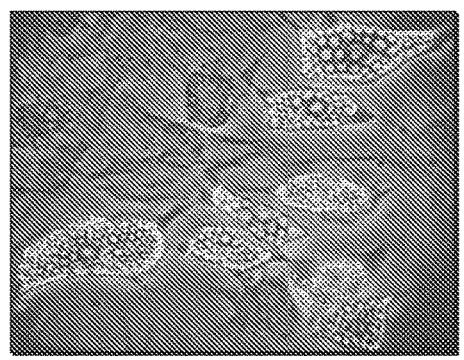
FIG. 4 shows MSCs differentiate towards adipogenic (A) and osteogenic (B) lineages after thawing and expanding the cryopreserved MSC.
Figure 4B:
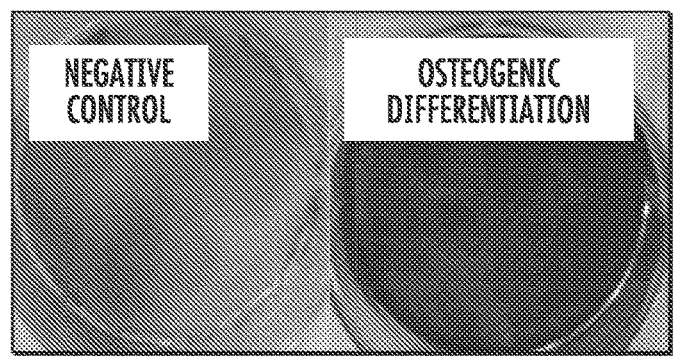

Expanded hMSCs were differentiated towards adipogenesis (fat) and osteogenesis (bone) in bulk culture (FIG. 4). Commercially available kits were used to differentiate MSC to adipocytes and osteoblasts (StemPro® Adipogenesis and Osteogenesis Differentiation Kits, Life Technologies®) using the protocols provided. Differentiation was detected by Oil Red 0 staining of lipid vesicles for adipogenesis (FIG. 4A) and Alizarin Red stain (FIG. 4B) of calcium for osteogenesis.

Figure 5:
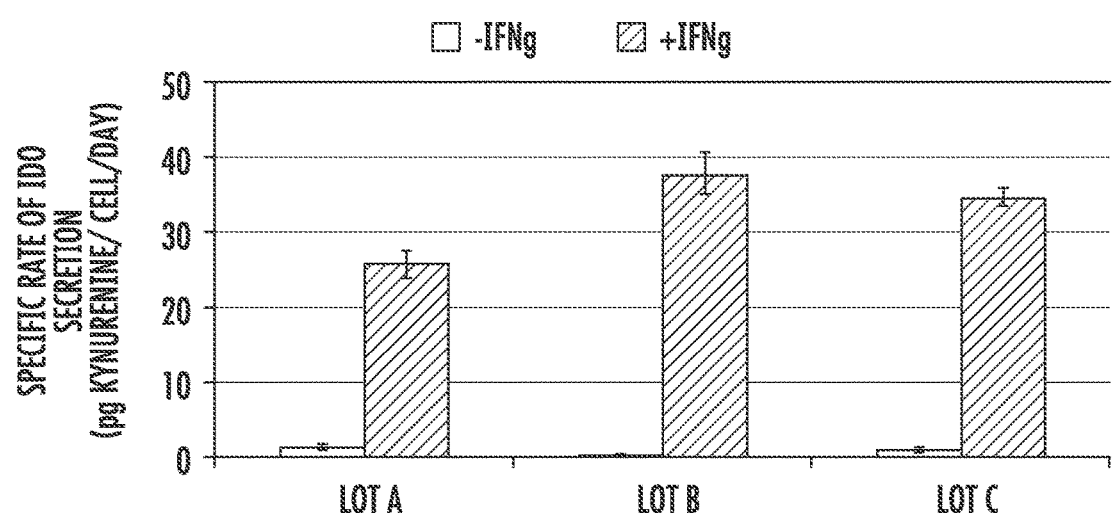
FIG. 5 is a bar graph showing MSCs maintained their immunomodulatory function after thawing and expanding the cryopreserved MSCs.

Induction of indoleamine 2,3-dioxygenase (IDO) expression and activity by exposure of the MSC to IFN-γ is central to the immune suppressor function (T-cell suppression) of human MSCs (FIG. 5). Briefly, MSCs were plated in media at 40,000 cells/cm$^2$ with or without IFN-γ. After 24 hr of incubation, media supernatant was collected and frozen. IDO activity was measured by quantifying kynurenine, the product of IDO enzymatic activity, using a standard colorimetric assay.

MSCs are commercially available from multiple vendors and can be distributed in a biopreserved format (typically cryopreserved). The cells after biopreservation can be plated into culture where they first adhere, and then grow. These cells are capable of expressing various therapeutically relevant functions such as multilineage differentiation, the secretion of bio-functional cytokines and factors, and can be induced to modulate the immune system.

Figure 6A:
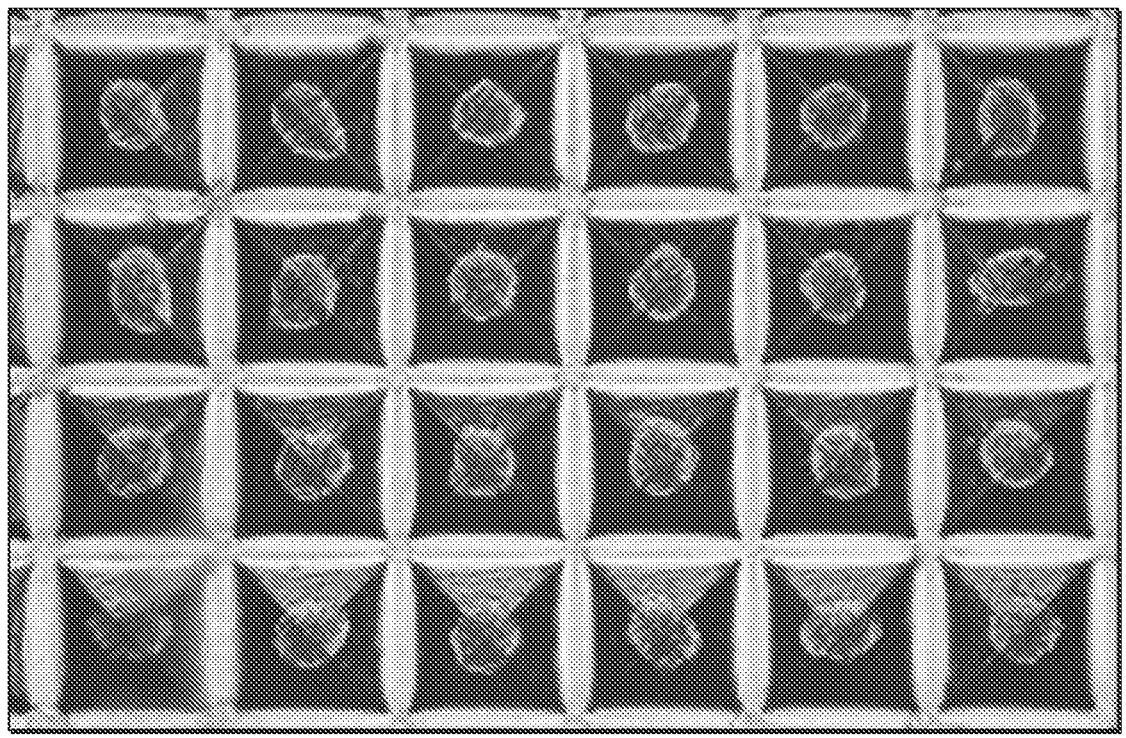
FIGS. 6A and 6B are images showing hMSC aggregate formation.
Figure 6B:
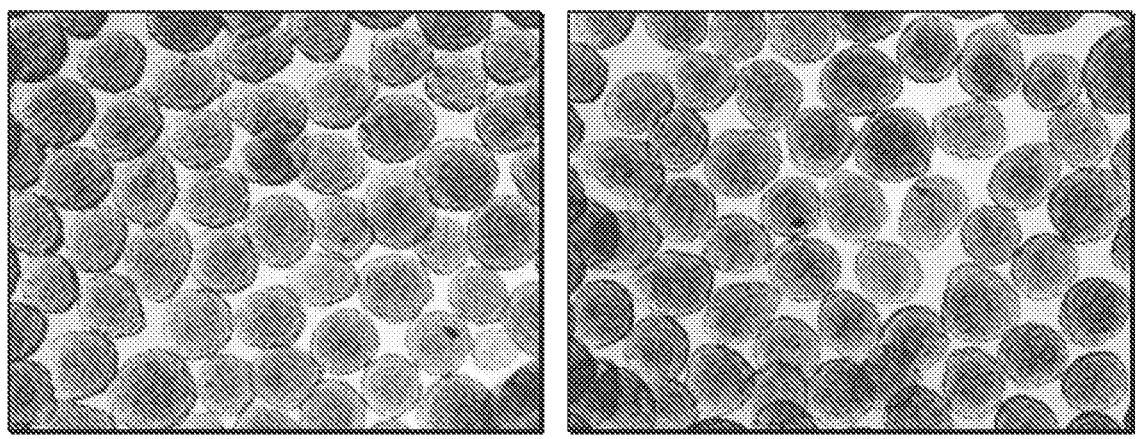

Example 2: MSC Aggregate Formation & Characterization hBM-MSCs (RoosterBio®, Frederick, Md., part # MSC001) were thawed and plated into T225 flasks in RoosterBio® growth media and cultured for 4-5 days until 80-90% confluent, or seeded directly after thawing into Aggrewell™ 400Ex plates (Stem Cell Technologies) in growth media (RoosterBio®). For cell expansion prior to aggregates formation, cells are seeded at 3000 cells/cm2 and incubated in 37oC incubator until ready for harvest. Cells were harvested with TrypLE (Thermo Fisher®) and plated into Aggrewell™ 400Ex in RoosterBio® growth media at a density of 1000 cells per aggregates. Aggrewells™ were rinsed once with rinsing solution prior to use according to manufacturer's instruction. Rinsing solution was aspirated and single cells were seeded drop by drop into each microwells to ensure even cell distribution. Overnight, hMSCs fused and formed multicellular aggregates (aggs) (FIG. 6A) in each microwell in 37oC incubation. Aggregates were collected from the wells by rinsing with growth media and transferred into 50 ml conical tubes. Concentrated aggregates (FIG. 6B) were obtained by aspirating the growth media in tubes after allowing aggregates to settle on the bottom of tube by gravity. It is common to require 100,000 to 1,000,000 aggregates of 1000-100,000 cells per aggregate to run an experiment or create a clinical-sized piece of tissue.

Figure 7A:
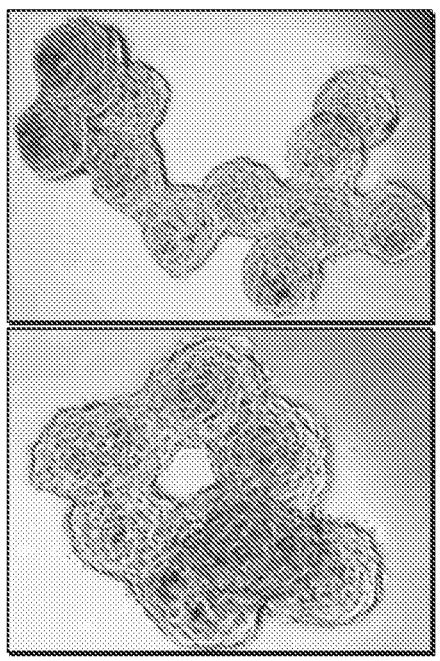
FIG. 7A are images showing MSC aggregate spontaneous fusion indicating living and metabolically active cells.
Figure 7B:
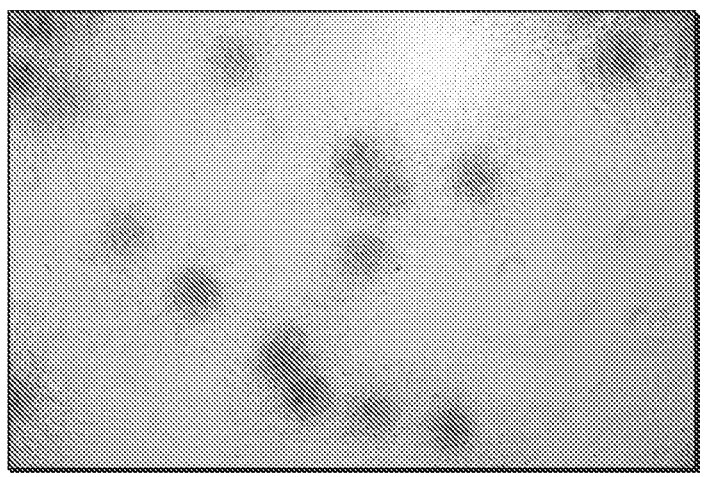
FIG. 7B shows MSC aggregate attachment indicating living and metabolically active cells.

Freshly collected hMSC aggregates were plated into non-adherent petri dishes or plates to culture the multicellular aggregates. The aggregates will quickly fuse together if seeded in non-adherent culture plates (FIG. 7A), and if seeded into tissue culture (TC) plastic the aggs will attach to the plate and the individual cells will grow out onto the dish (FIG. 7B). Cultures were incubated in 37° C. incubator overnight before images were taken.

Figure 8:
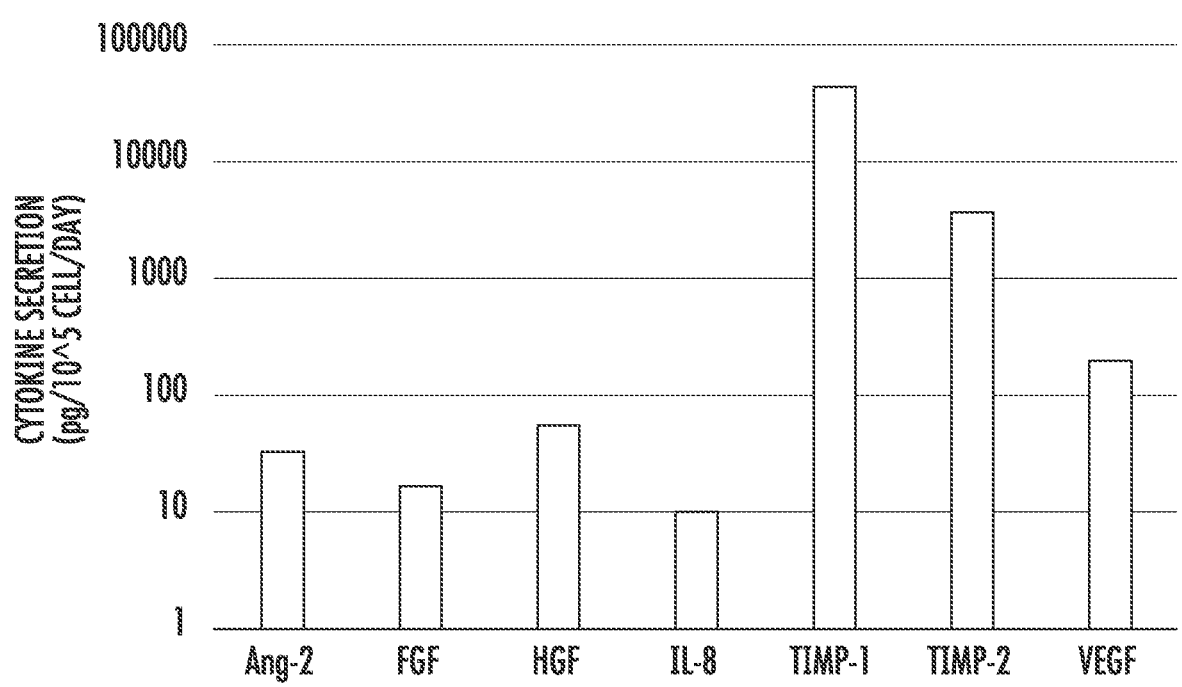
FIG. 8 is a bar graph showing MSC aggregates continue to secrete angiogenic cytokines when plated and incubated in 37° C. culture.
Figure 9:
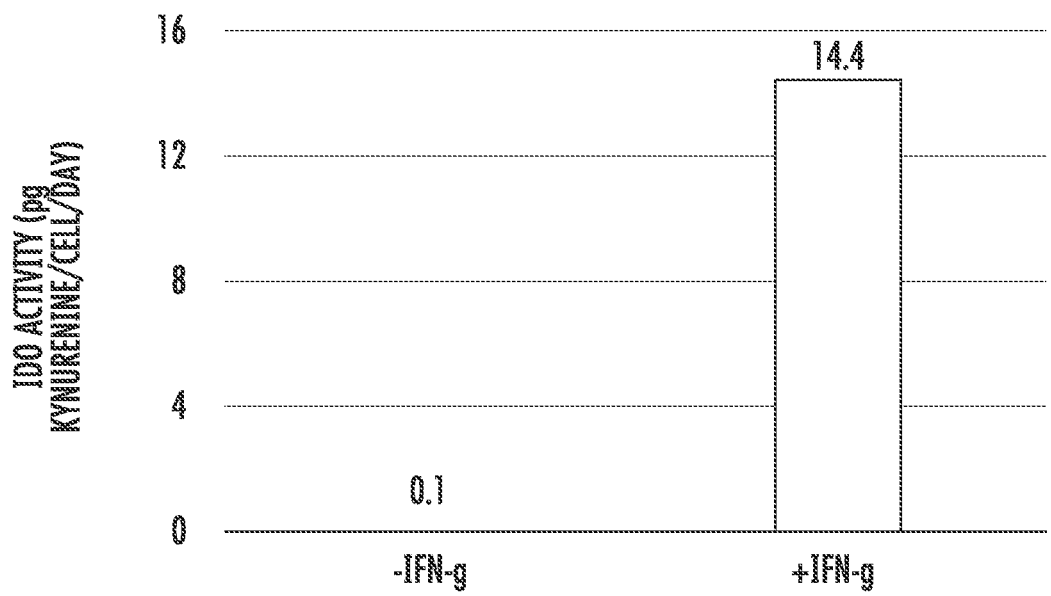
FIG. 9 is a bar graph showing Indoleamine-pyrrole 2,3-dioxygenase (IDO) activity of MSC aggregates.

The MSC aggregates were seeded into plates for cytokine analysis and incubated at 37° C. for 24 hours, +/−1 hour, at which time the cell culture media was collected at frozen at −20° C. The collected media was then assayed using the Q-Plex™ Human Angiogenesis (9-plex, Quansys Biosystmes) fully quantitative ELISA-based chemiluminescent assay allowing the concurrent measurement of the nine angiogenic biomarkers ANG-2, FGF basic, HGF, IL-8, TIMP-1, TIMP-2, TNFα, VEGF. The multiplexed ELISA provides analytes in pg/mL in the culture supernatant, which was then normalized to the number of cells seeded into the wells and time in culture to obtain a specific cytokine secretion metric in pg/cell/day (FIG. 8). The MSC aggregates were also capable of maintaining the ability to upregulate IDO activity in the presence of interferon gamma.

This Example demonstrates that hMSCs can be formed into aggregates, either after cell expansion or directly out of thaw. The cells maintain their ability to adhere to culture plastic and fuse, which are key attributes to MSC aggregates. The cells within the aggregates also maintain functions such as multilineage differentiation, cytokine secretion, and immunomodulation.

Figure 10A:
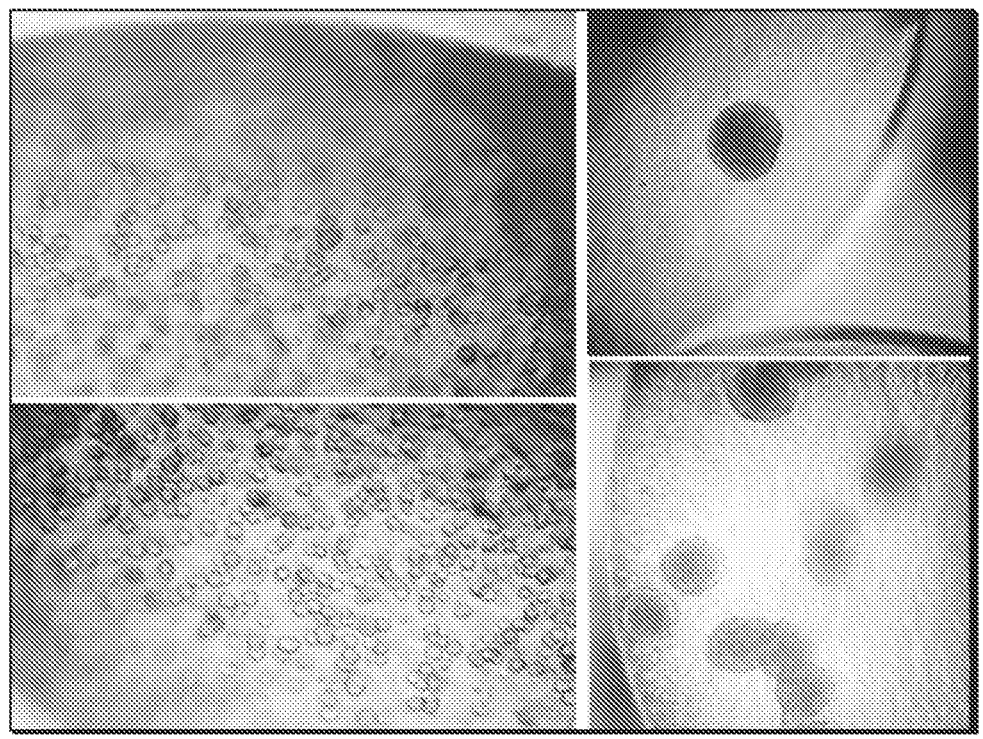
FIG. 10A is an image showing single cell and aggregate MSC encapsulated in alginate and extruded into CaCl2.
Figure 10B:
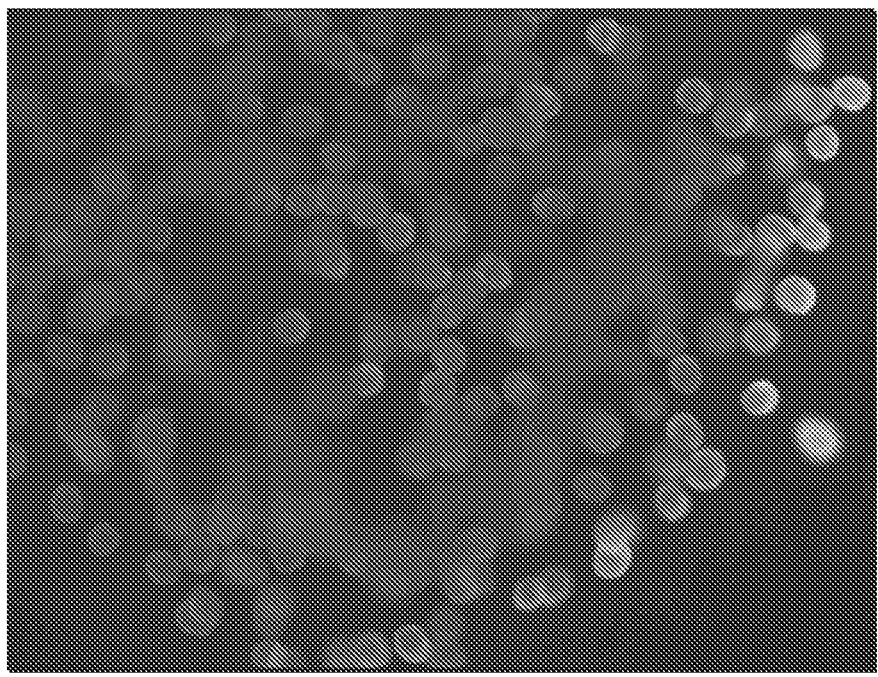
FIG. 10B is an image showing highly viable MSC aggregates that were stained with Calcein-AM after enacapsulation (green.
Figure 10C:
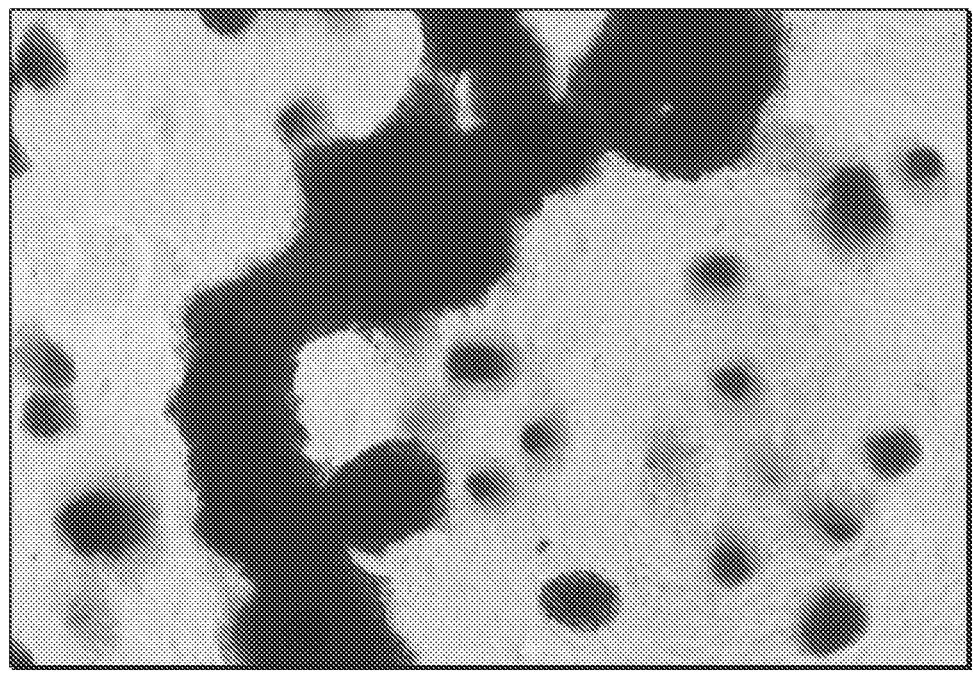
FIG. 10C is an image showing fusion of MSC aggregates in extruded alginate.

Example 3: Aggregates Encapsulation in Hydrogel and Extrusion of Custom Construct For cell encapsulation, single cell hMSCs or freshly collected hMSC aggregates were suspended in 2% alginate (FMC BioPolymer) dissolved in DPBS without $Ca^{2+}$ or $Mg^{2+}$. Cells were extruded, drop by drop with needle into 6.6 mg/ml of $CaCL_2$ solution to form spherical beads or extruded into custom shapes on petri dish, before submerged in $CaCl_2$ solution to allow for cross-linking of the construct. $CaCl_2$ solution were aspirated and replaced with growthmedia before incubating the construct in 37° C. incubator for cell to mature. The encapsulated MSCs were stained with 2 µM Calcein-AM/DPBS and imaged with fluorescence microscope which show highly viable aggregates within the alginate gels (FIG. 10B). These aggregates also maintained their ability to fuse in the gels (FIG. 10C) after 5 days in culture.

Results and Discussion:

MSC Aggregates are attractive configuration for bioprinting due to the ease of printing as well as the higher chance of cells survival when aggregated. Highly viable hMSC aggregates are shown that they can be consistently generated using Aggrewell™ plates. These aggregates have the ability to fuse together and attach onto surface to proliferate, both are key functional parameter of metabolically active cells. Aggregates fusion was observed as early as a few hours post incubation in media at 37° C. for freshly collected aggregates.

Since bioprinting application require cells to be embedded in cell compatible biomaterials, we demonstrated that single cell and aggregate MSCs encapsulated in 2% alginate and extruded into custom shapes were highly viable (FIG. 10B), and they maintained their ability to fuse in culture (FIG. 10C), hence confirming the feasibility of aggregate cells to be used for biofabrication and bioprinting applications.

While this new product format has been used in research, many of the practical aspects of delivering these cells in an aggregated format have not been worked out. Many in the field assume that the cells will be harvested, made into aggregates and then used immediately. However, for wide spread adoption, the technology has to be developed to enable MSC aggregates to be available for use immediately. Essentially, biopreservation technologies must be adapted to MSC aggregates and their critical functions must be maintained.

Disclosed here is an optimal process for biopreservation of hMSC aggregates, an outline of the economic and practical benefits of having "ready to use" formulations, and demonstration of its usefulness. As MSCs, and other cells, used on an aggregated format requires hundreds of millions to billions of cells, standard technology would require several weeks just to generate the cells using cell expansion technology that is not wide spread. Formulations of high cell numbers, delivered as aggregates, is disclosed as a way to decrease the significant timeframes (weeks to months) down to immediate use. These "ready to use" formulations can have significant economic impact on the labs performing the work, and can lead to more rapid discoveries and product development efforts.

Example 4: Biopreserved MSC Aggregates

It is the goal of this example to demonstrate that aggregates can be biopreserved and still retain critical functions. Here, aggregates were tested after being stored in a non-frozen format in cell culture media (RoosterBio® part # KT-001), a clinical gold standard storage solution for cell therapy, Normal Saline+4% HSA (BioMed Supply®), and Hypothermosol® (Biolife Solutions®). The ability to preserve MSC aggregate functions over days in non-frozen storage, or weeks to years in cryopreserved formats, will be central to the commercialization and ease of use of this technology in the future, and will save researchers and product developers weeks of time if MSC aggregates can be purchased in a ready-to-use format.

Materials & Method hBM-MSCs (RoosterBio®, Frederick, Md., part # MSC001) were thawed and plated into T225 flasks in RoosterBio™® growth media (RoosterBio® Inc) and cultured for 4-5 days until 80-90% confluent, or seeded directly after thawing into Aggrewell™ 400Ex plates (Stem Cell Technologies) in RoosterBio™® growth media (RoosterBio® Inc.). For cell expansion prior to aggregates formation, cells were seeded at 3,000 cells/cm$^2$ and incubated in 37° C. incubator until ready for harvest. Cells were harvested with TrypLE and plated into Aggrewell™ 400Ex in RoosterBio™® growth media at a density of 1,000 cells per aggregates. Aggrewell™ were rinsed once with rinsing solution prior to use according to manufacturer's instruction. Rinsing solution was aspirated and single cells were seeded drop by drop into each microwells to ensure even cell distribution. Overnight, hMSCs fused and formed multicellular aggregates (FIG. 6A) in each microwell in 37° C. incubation. Aggregates were collected from the wells by rinsing with growth media and transferred into 50 ml conical tubes. Concentrated aggregates (FIG. 6B) were obtained by aspirating the growth media in tubes after allowing aggregates to settle on the bottom of tube by gravity.

Freshly collected aggregates were resuspended at 1500 aggs/ml of storage solution (i.e., Hypothermosol®, 10% FBS/DMEM or 4% HSA/saline). Aggregates in respective solution were alliquoted into 2 ml cryovials and stored in 4° C. refrigerator in dark.

Aggregates Functionality (Fusion, Cells Adhere to Dish, IDO and Cytokine Secretion)

On day 3 or 7 of study, aggregates from different conditions were collected and rinsed once with PBS, and 250 aggregates (OR 250,000 cells) were resuspended and seeded into each well of 12-well plate in 2% FBS/basal media, with or without 10 ng/ml IFN-γ. Additional aggregates were collected and plated onto non-adherent 48-well plate to allow for spontaneous fusion. After 24 hours (FIG. 11) and after 6 days (FIG. 12) of incubation, images were taken on cells that were both adherent on tissue culture plate, or fused while floating on non-adherent surface. The media on adherent cultures were collected into 15 ml centrifuge tubes for IDO and cytokine secretion assay. Aggregates that were plated on the tissue culture plate were treated with 250 μl of trypsin/EDTA and mixed by pipetting every 10-15 min for 45 min to release cells from aggregates. Dissociated cells were enumerated with NucleoCounter® for total viable cell count.

For measurement of cytokine secretion, the collected supernatant was assayed using the Q-Plex™ Human Angiogenesis (9-plex, Quansys Biosystems®) fully quantitative ELISA-based chemiluminescent assay allowing the concurrent measurement of the nine angiogenic biomarkers ANG-2, FGF basic, HGF, IL-8, TIMP-1, TIMP-2, TNFα, VEGF. The multiplexed ELISA provides analytes in pg/mL in the culture supernatant, which was then normalized to the number of cells seeded into the wells and time in culture to obtain a specific cytokine secretion metric in pg/cell/day.

For measurement of IDO activity, the amount of kynurenine was measured using a standard colorimetric assay as described in Example 1 above.

Figure 11:
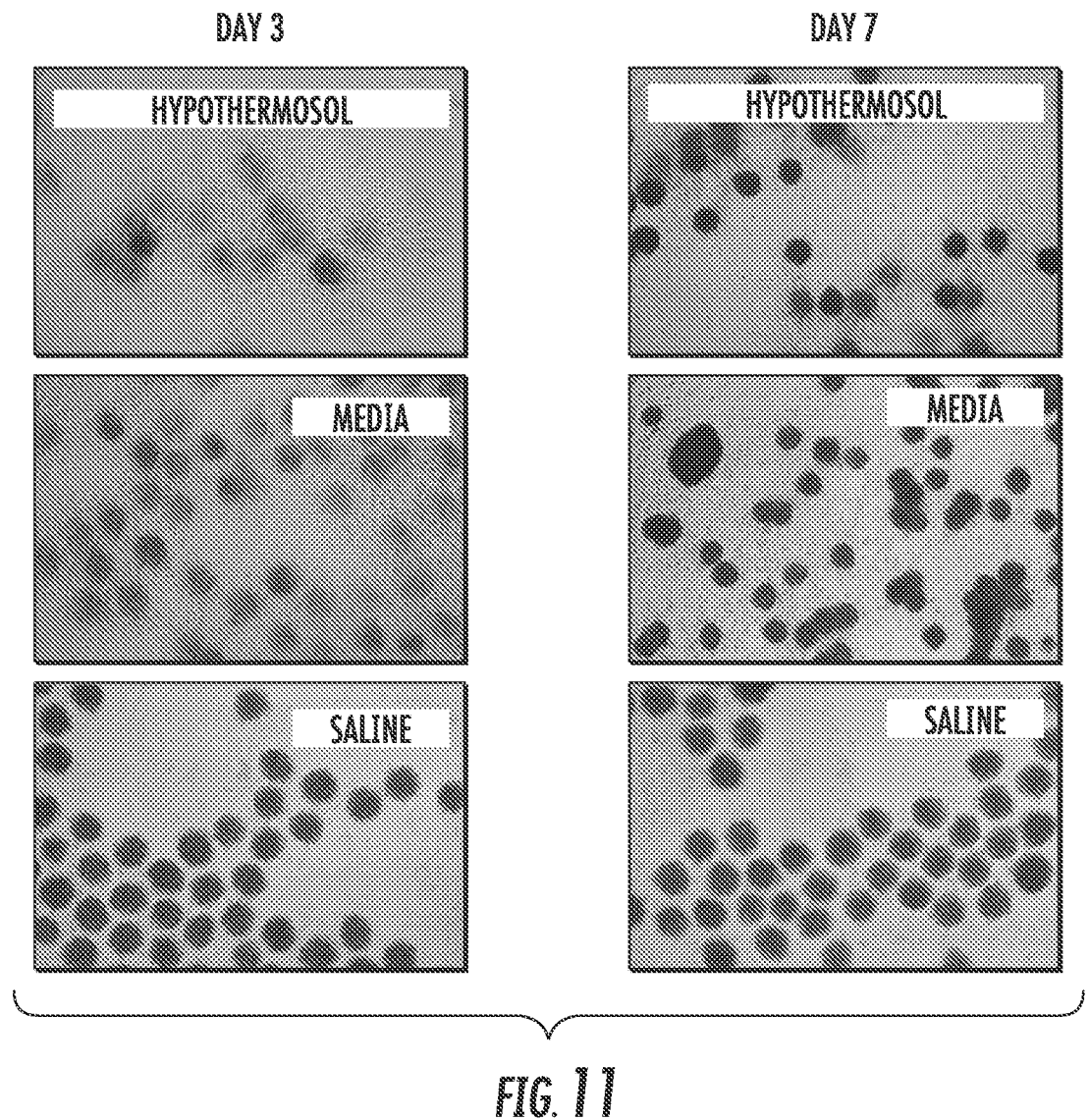
FIG. 11 is a series of images showing hMSC aggregates stored for 3 and 7 days at 4° C. in Hypothermosol®, media, or saline with 4% HSA, 1 day after culture in TC plate.
Figure 12:
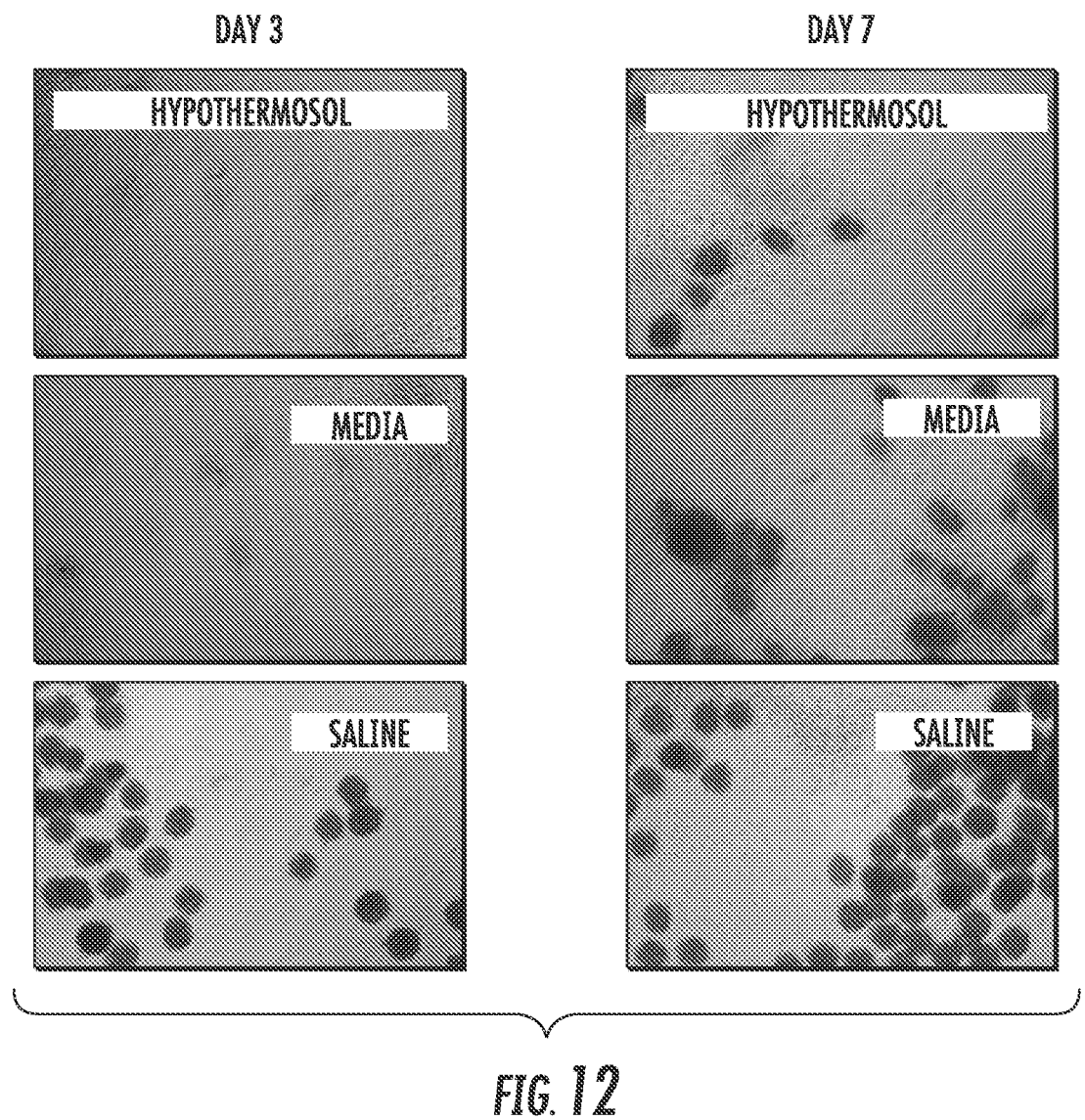
FIG. 12 is a series of images showing hMSC aggregates stored for 3 and 7 days at 4° C. in Hypothermosol®, media, or saline with 4% HSA, 6 days after culture in TC plate.
Figure 13:
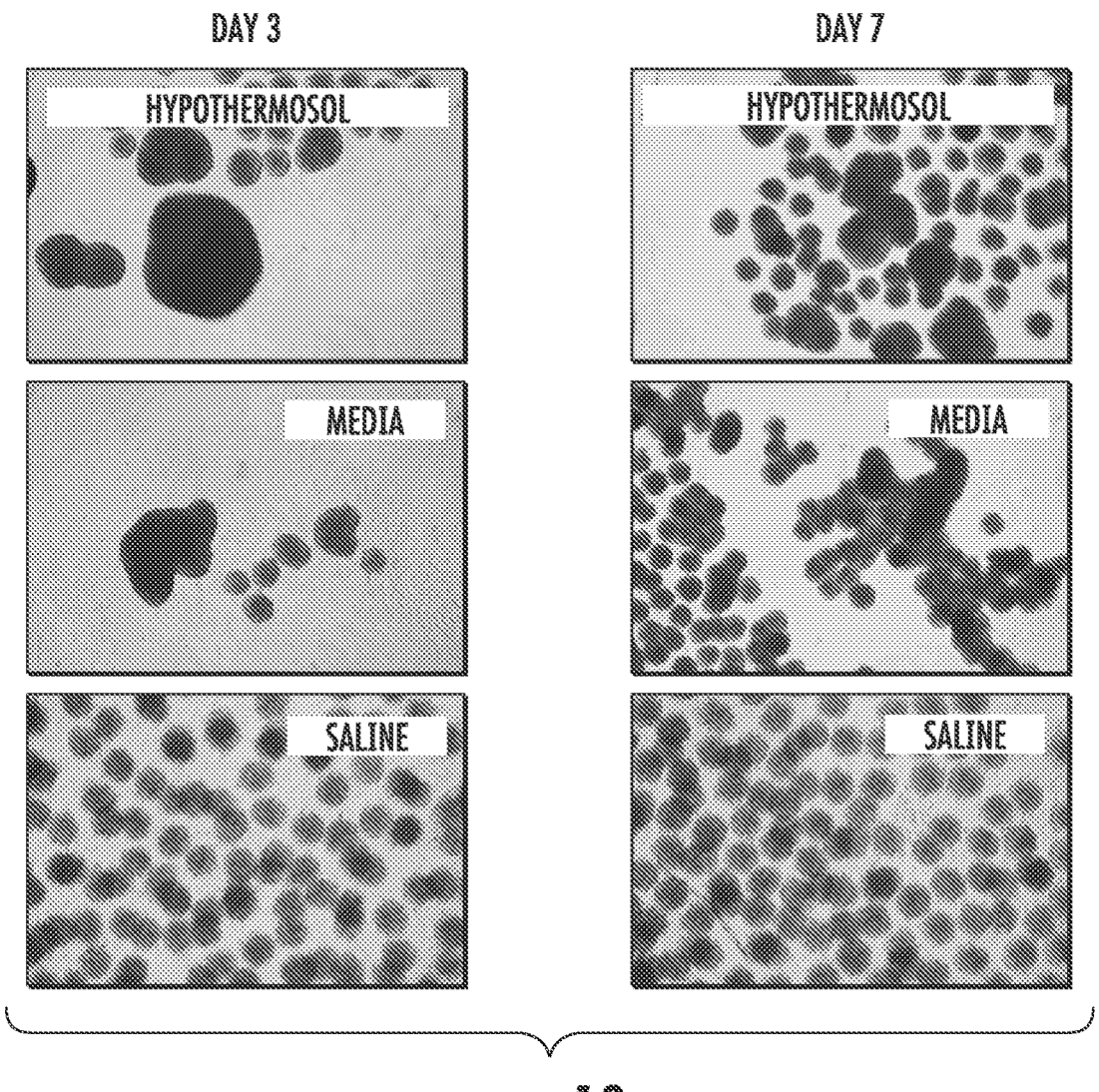
FIG. 13 is a series of images showing hMSC aggregates stored for 3 and 7 days at 4° C. in Hypothermosol®, media, or saline with 4% HSA, 1 day after culture in non-adherent plate.

Results & Discussion:

Since bioprinting applications require the cells to remain highly viable prior to printing, it is preferable that the aggregates can be stored in hypothermic condition for a period of time (1-7 days), without affecting the viability and functionality of the cells. FIG. 11-13 shows the ability of aggregates to (A) fuse or (B) attach, after 3 or 7 days storage in Hypothermosol® solution, growth media, or saline with 4% HSA. Similar degree of fusion and adhesion was observed in aggregates stored in both in Hypothermosol® and growth media, however, aggregates formulated in 4% HSA/saline did not survive, as indicated by floating and loose aggregates structure. After 6 days in culture (FIG. 12), aggregates that adhered on the TC plates continued to proliferate in the plates to confluent demonstrating that the cells remained metabolically active.

Figure 14:
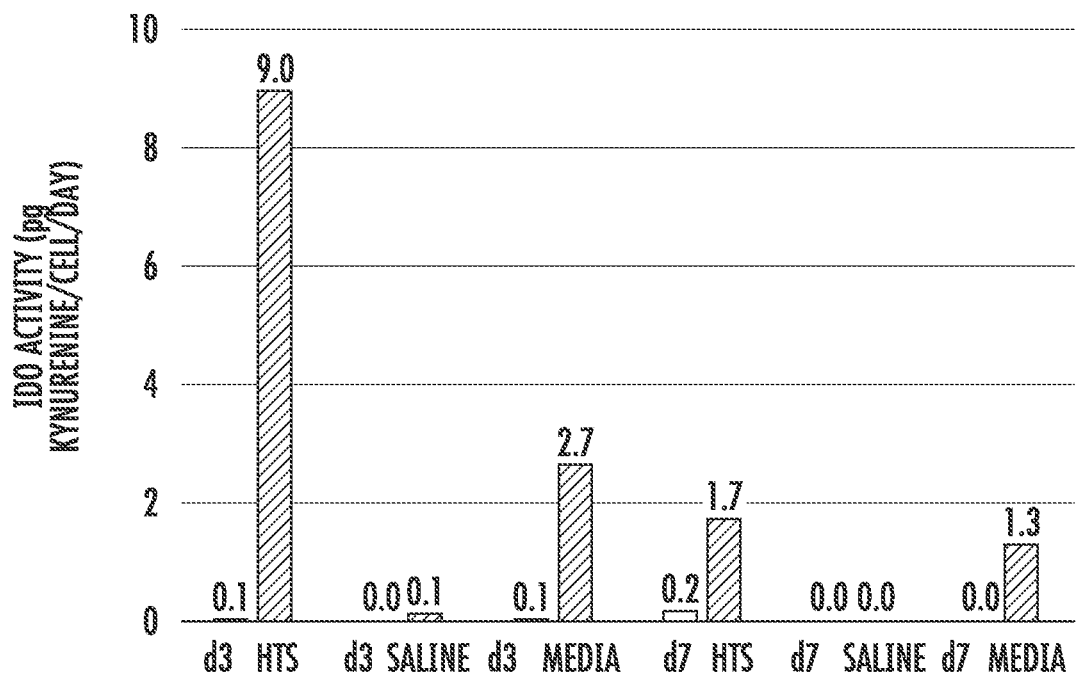
FIG. 14 is a bar graph showing IDO activity by MSC aggregates after storage in HTS, saline, media for 3 or 7 days at 4° C.
Figure 15:
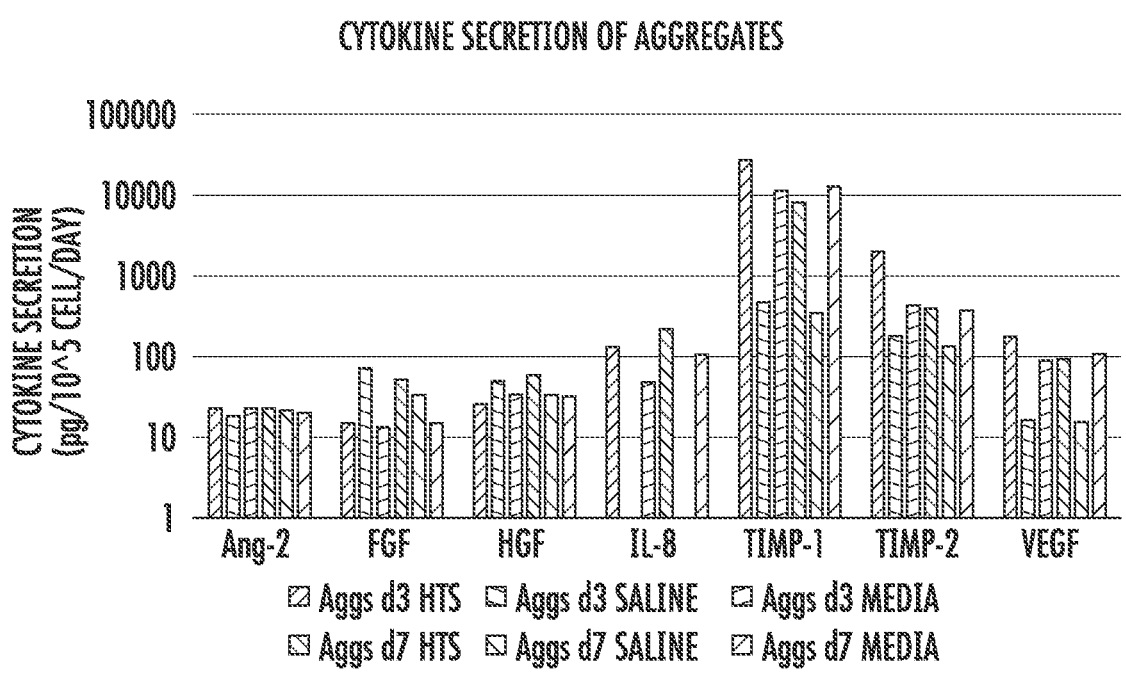
FIG. 15 is a bar graph showing Ang-2, FGF, HGF, IL-8, TIMP-1, TIMP-2, and VEGF secretion by MSC aggregates after storage in HTS, saline, media for 3 or 7 days at 4° C.

IDO activity (FIG. 14) and cytokine secretion (FIG. 15) of the biopreserved aggregates in the various formulation and storage duration show that they maintained their functionality, although this study suggest that aggregates biopreserved in Hypothermosol® solution outperformed the Growth media and 4% HSA/saline storage solution.

Example 5: MSC Aggregate Cryopreservation and Post-Thaw Function hMSC aggregates (1000 cells/agg) were prepared with Aggrewell™ 400EX as described above. Freshly collected aggregates were reconstituted in CryoStor®5 (Biolife Solutions®) at 1-5M cells/ml. Aggregates were frozen in a CoolCell® controlled rate freezing device (Biocision®) overnight and transferred into vapor phase liquid nitrogen for storage. After at least 7 days of cryopreservation, 2 vials of MSC aggs were thawed into 2% FBS/basal media and seeded onto tissue culture plate or non-adherent plate for testing for aggregate fusion, cell adhesion, and IDO and cytokine function assays (as described above).

To demonstrate aggregates viability, approximately 250,000 aggregates were used to fabricate a 'ring' shape in 15 ml tubes, by seeding the aggregates around a 20 μl pipette tip. Fused MSC aggregates were collected after 1-4 days and fixed with 4% paraformaldehyde, before the samples are dehydrated and stained for hematoxylin and eosin (H&E) (Alizee Pathology®) to visualize the compactness of aggregates fusion.

Results

Figure 16A:
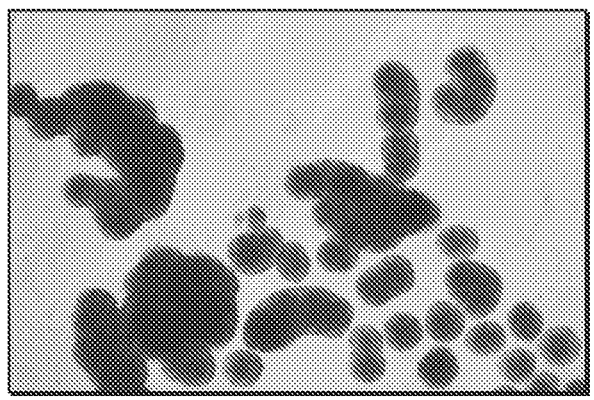
FIG. 16 is a series of images showing cryopreserved hMSC aggregates maintain the ability of aggregate fusion, and the ability of the individual cells to attach to tissue culture (TC) plastic and grow out of the aggregates.
Figure 16B:
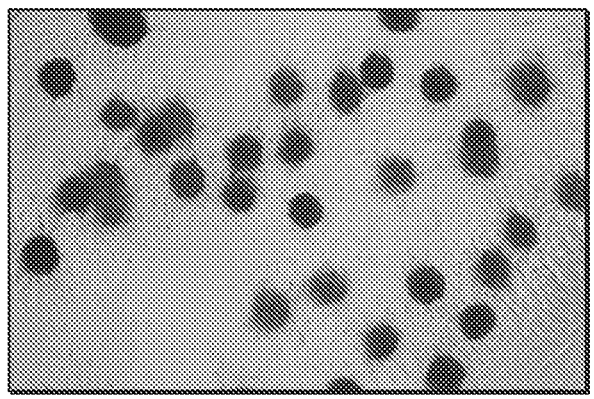
Figure 16C:
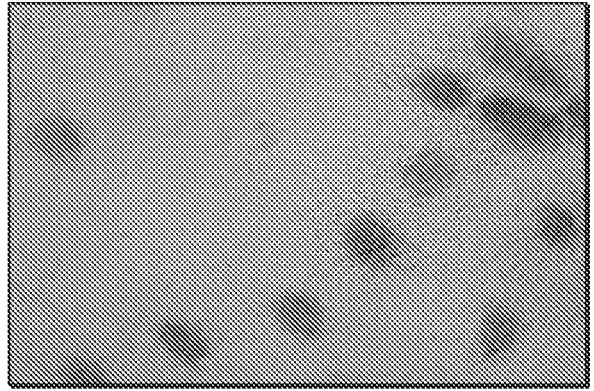
Figure 17:
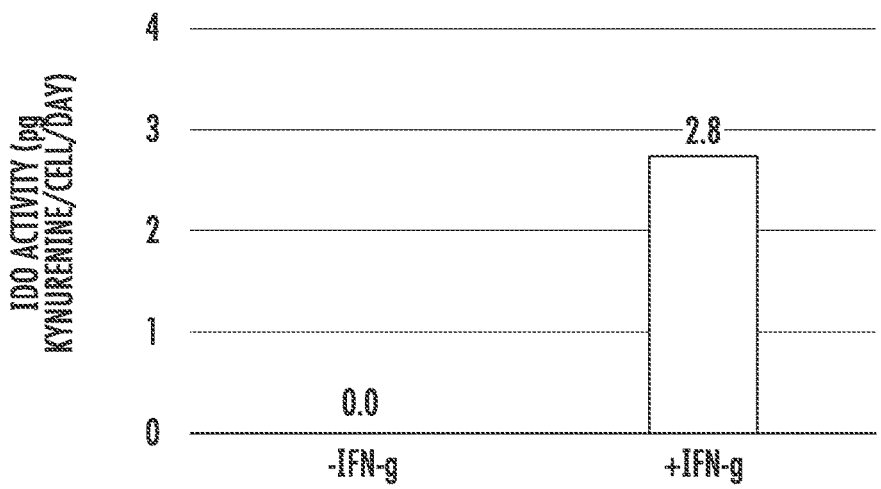
FIG. 17 is a bar graph showing cryopreserved aggregates maintain an inducible immunomodulatory phenotype.
Figure 18:
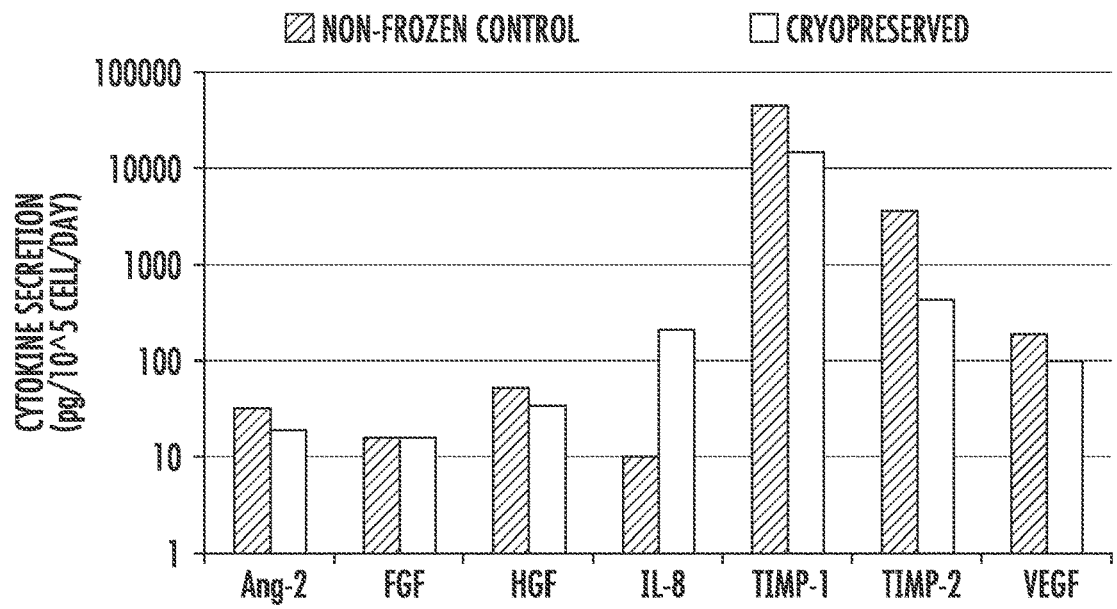
FIG. 18 is a bar graph showing Ang-2, FGF, HGF, IL-8, TIMP-1, TIMP-2, and VEGF secretion of cryopreserved and non-frozen MSC aggregates.
Figure 19A:
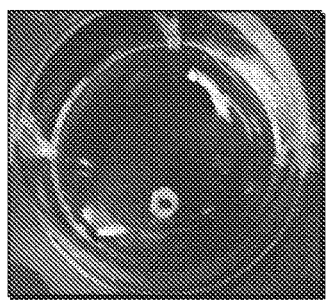
FIGS. 19A to 19C are images showing cryopreserved MSC aggregates were able to be fabricated into a ring shape (FIGS. 19A-19B), and H&E staining demonstrates consistent healthy fusion of aggregates throughout the ring structure (FIG. 19C).
Figure 19B:
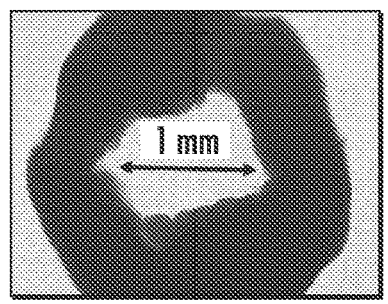
Figure 19C:
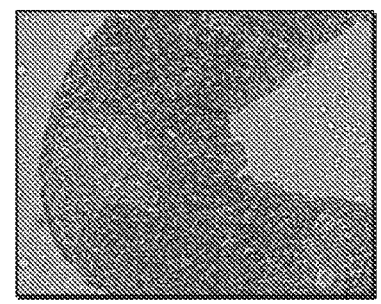

Upon thaw, hMSC aggregates were capable of maintaining the ability to fuse together (FIG. 16A), and the individual cells were capable of attaching to tissue culture plastic and grow out of the aggregates (FIGS. 16B and 16C). Furthermore, hMSC aggregates maintained the ability to have inducible IDO expressions (FIG. 17) as well as secrete angiogenic cytokines (FIG. 18). The frozen aggregates can be fabricated to form macroscopic shapes such as rings (FIGS. 19A and 19B) and H&E staining (FIG. 19C) demonstrates healthy macroscopic tissue formed out of fused aggregates that have been cryopreserved.

Discussion

Figure 20A:
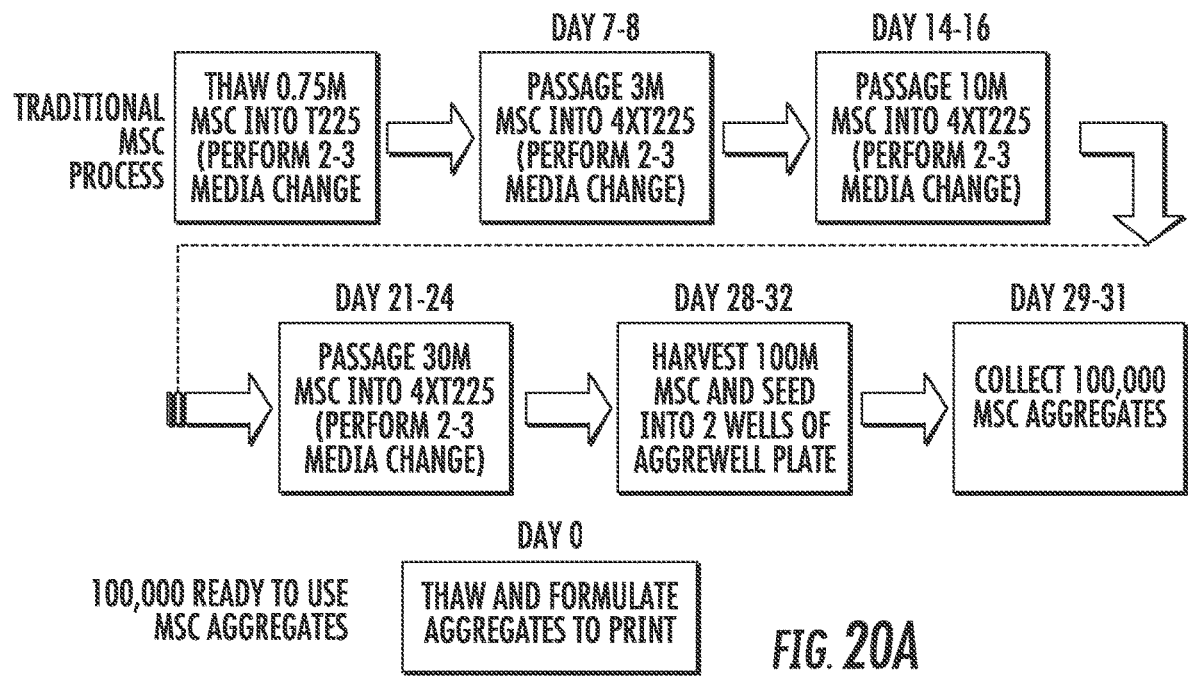
FIG. 20A is a process flowchart illustrating generation of 100,000 aggregates made with 1000 cells per aggregate.
Figure 20B:
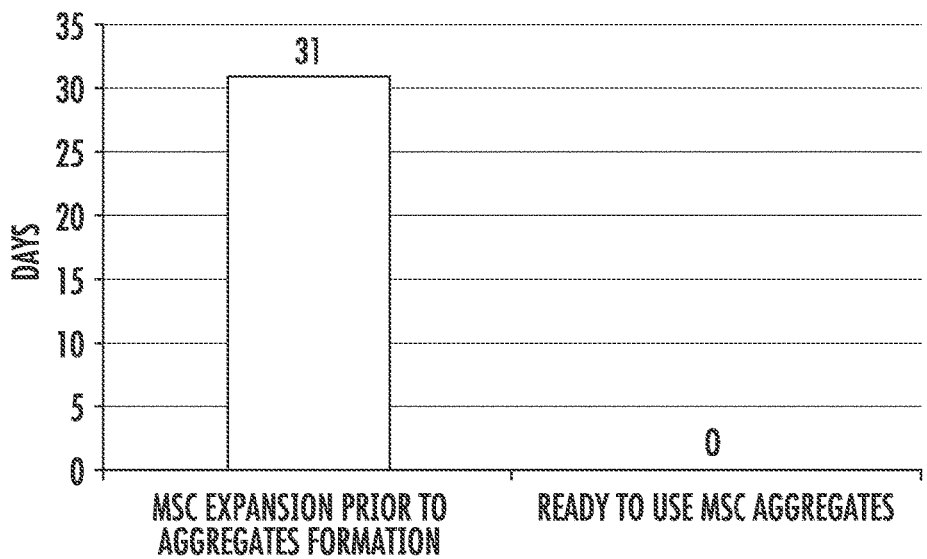
FIG. 20B is a bar graph showing time savings (days) for cell expansion.

This is the first example demonstrating that hMSC aggregates can be cryopreserved. Furthermore, the critical functions of hMSC aggregates are maintained post cryopreservation, including the ability of individual cells to grow out of aggregates onto TC plastic, the ability of aggregates to fuse into larger macroscopic tissues, and the cells ability to secrete cytokines and maintain their inducible IDO activity. A benefit of this new cryopreserved composition is their practicality where cryopreserved product formats bring off the shelve, on-demand supply of aggregate cells compared to complex and lengthy preparation steps required to make fresh aggregates. The flexibility to thaw and use the aggregates as needed, saves a researcher or clinician weeks to months of cell culture time as shown in the process flow diagram in FIG. 20A. When transferred to a cGMP manufacturing facility—the amount of time savings translates into tens of thousands of dollars (FIG. 20B).

Example 6: Alginate BioInk Development

Figures 21A, 21B, 22:
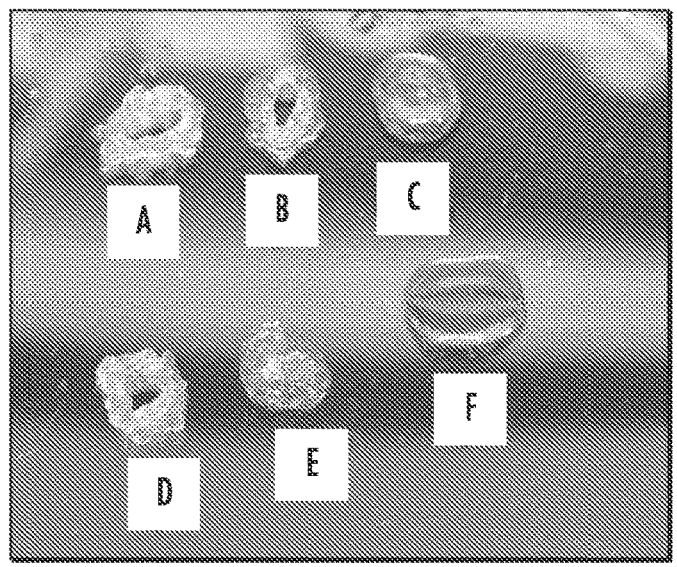
FIG. 21A is an image showing printability testing of different alginate formulations.
FIG. 21B is a chart showing consistency and tackiness of different alginate formulations.
FIG. 22 is a chart showing settling and clumping of different alginate formulations.

A bioink need to comprise of cells with biocompatible hydrogel matrix to suspend either single cell or aggregates in homogeneous suspensions during storage to prevent cell clumping and to maintain cell concentration homogeneity. High viscosity high M and high G alginates were tested, including low viscosity alginates, against 2 different calcium sources ($CaCl_2$ and $CaSO_4$). The amount of calcium in the hydrogel matrix could dictate the degree of cross-linking of hydrogel, hence the structure and integrity of printed construct. In this study, the amount of $CaSO_4$ that allow sufficient gelling to formulate cells was titrated for the best printability due to its slow releasing action, allowing a reasonable 'time window' for users to manipulate and mix the solution prior to the gelling. Here, we show that high G alginates of medium to high viscosity can be used to make bioinks with good "printability", i.e. the ability to maintain "semi-solid" structure (characterized by the ease of extrusion out of a nozzle, thickness of gel that is sufficient to hold shape in place, but not too solid that it crumbles) and tacky, which is the ability of the gel to stick and integrate onto itself for building multi-layer shapes. The right formulation will also allow for aggregates to remain in homogenous solution during storage to avoid settling and clumping (FIG. 22), which could clog the print head. Finally $CaCl_2$ washing treatment after printing strengthens the shapes and enables preservation of structure while cells mature.

Methods:

2-8% medium viscosity (Sigma Aldrich) or high viscosity (FMC Biopolymer) alginate with high G (protanal) or high M (manugel & sodium alginate from Sigma) were prepared in DPBS without $Ca2+$ or $Mg2+$. 25 mg/ml $CaSO_4$ was prepared in DPBS and used for gelling the alginate to the right consistency. Different volume of alginate was used, i.e. 10% v/v/, 5% v/v, or 2.5% v/v was tested with the different alginate types and the gels incubated overnight to determine the degree of 'gelation' and 'printability'.

Results:

Low viscosity alginates did not crosslink well enough to partially gel the structure even at alginate concentrations up to 8%. Medium/high viscosity alginates (Manugel a high M alginate and Protanal a high G alginate used here) were more suitable and shown to make good printable formulations. Calcium chloride was not optimal as a divalent cation source, so calcium sulfate was used to more slowly release calcium into the mixture—creating a more homogeneous hydrogel. Higher levels of calcium sulfate in the high G alginate led to gel that is too rigid which crumbled when extruded out of the syringe needle assembly. Intermediate levels of calcium sulfate (1.25 mg/mL mixed in 2% protanal) was ideal, giving the alginate a smooth ejection consistency, the ability to build up multiple layers, where the newly ejected alginate adhered to previously extruded material (tackiness) to form 3D structures. The low levels of calcium sulfate were not sufficient to gel the alginate and it was still fluid—not ideal for printing (FIG. 21).

After printing 3D structures, the printed structure were not immediately mechanically stable. "Curing" the printed structures with small volumes of dissolved calcium chloride created mechanically stable structures. The following process and formulation for bioink was identified: cells or cellular aggregates are mixed into 2% high G, medium to high viscosity alginate via syringe mixing (connect 2 syringes together with connector and mix 2-10 times); all solution is transfer to one syringe, and calcium sulfate added to a final concentration of 1.25 mg/mL, and mixed via syringe mixing; the alginate gel is allowed to sit for 5 minutes, or for as long as several weeks; a syringe, or other cartridge system, is placed on a 3D printer and a 3D tissue is printed; and printed tissue is placed in culture or bioreactor depending on application.

Figure 24A:
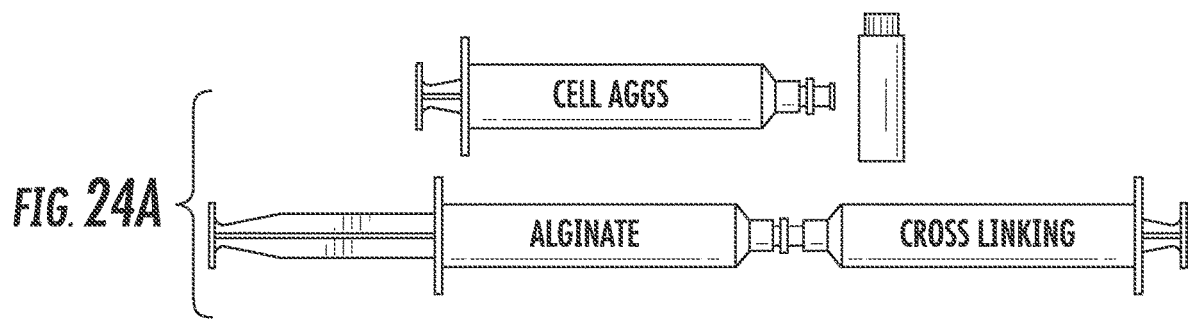
FIGS. 24A & 24B are images showing bioink kit for MSC aggregate product configuration.
Figure 24B:
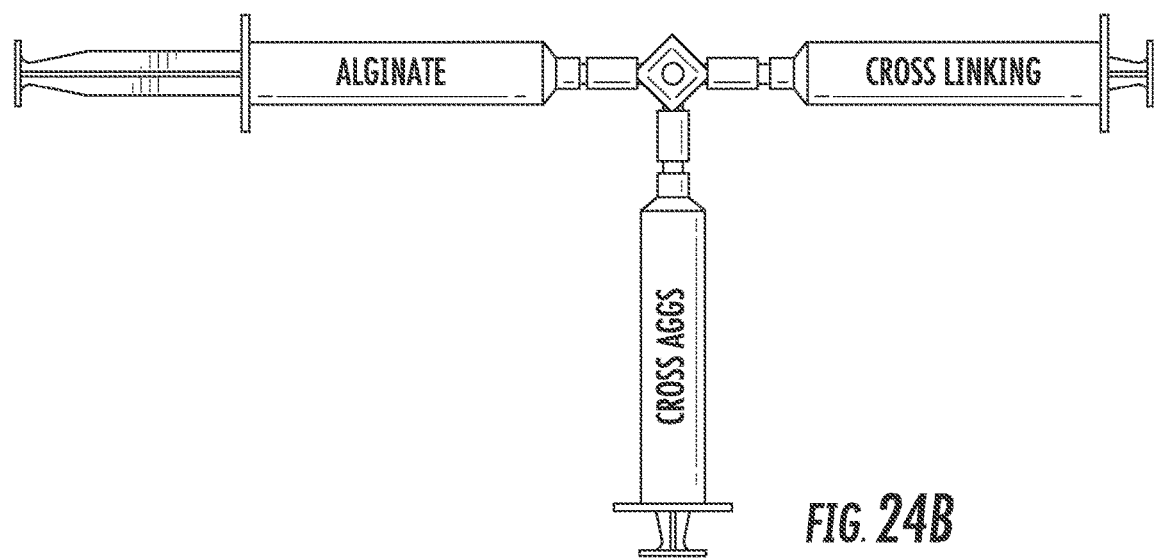

Thus, bioink kits are contemplated that contain a syringe, or other container, of non-gelled hydrogel polymer such as alginate; a sterile connect device allowing for 2 syringes to be connected sterilely; another syringe containing the cross-linking agent (e.g., calcium sulfate), and a third syringe containing cells or cellular aggregates (FIGS. 24A & 24B)

With this kit, it is possible for an end user to quickly, easily, and reproducibly create cellular containing bioink for various applications.

Figure 25:
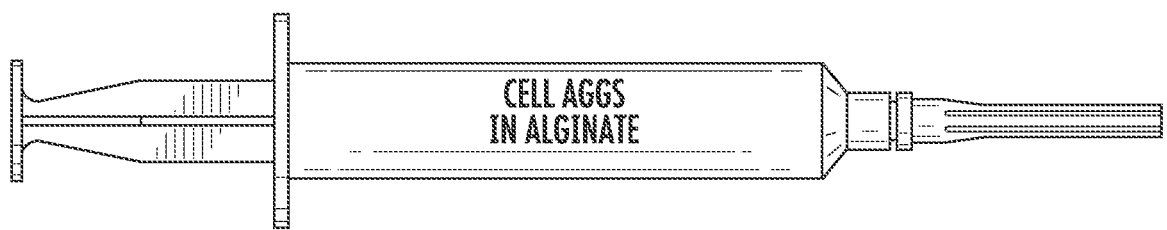
FIG. 25 is an image of final MSC aggregate bioink product configuration, suitable for product transportation and storage in 4° C.

In some cases, the bioink is gelled with the cells prior to shipping (FIG. 25), so that a customer can skip the above process altogether and insert the bioink containing cartridge into a 3D printer and directly print (Ready to Use)—saving considerable time.

Example 7: Alginate BioInk Biopreservation

Materials & Method

BioInk A Preparation

2% alginate in Hypothermosol® (BioLife Solutions®) was prepared by diluting 0.4 g protanal (high G alginate) in 20 ml Hypothermosol® with constant stirring. MSC aggregates were mixed into 2 ml alginate solution and 10% of 25 mg/ml $CaSO_4$ was added and mixed using syringe to allow for partial gelling. Syringe is sealed off with parafilm and stored in 4° C. in dark until ready for testing.

BioInk B Preparation

For alginate bioink with Hypothermosol & collagen, 3 mg/ml collagen (Collagen Solutions Inc.) was prepared according to manufacturer's instruction where 1 part of buffer solution was added into 9 part of collagen solution on ice and mixed well. For incorporation of aggregates with collagen and alginate, MSC aggregates were added to 1 ml of 3 mg/ml of collagen solution before mixing with equal volume of 2% alginate. Once solution is well mixed, 10% v/v of 25 mg/ml $CaSO_4$ was added with syringe and mixed well to partially gel the bioink solution. Similarly, the syringe was sealed off with parafilm and stored in 4° C. in dark until ready for testing.

After 2 weeks in storage, 50-100 µl of both Bioink A and B were extruded into 15 ml centrifuge tubes. 4 ml of 50 mM sodium citrate were added to the gel and incubated in 37° C. to dissolve the gel. Tubes were inverted every 10 mM for 30 mM until gel is dissolved. Cells were collected by centrifuging at 200×g for 5 mM. Supernatant was aspirated and cells resuspended into 2% FBS/basal media and plated into TC plates to allow for attachment.

For preparation of control cells, freshly thawed MSCs were incubated with 50 mM sodium citrate for 30 mM similar to the process for releasing MSCs from alginate before they were centrifuged and plated onto TC plate.

Figure 23:
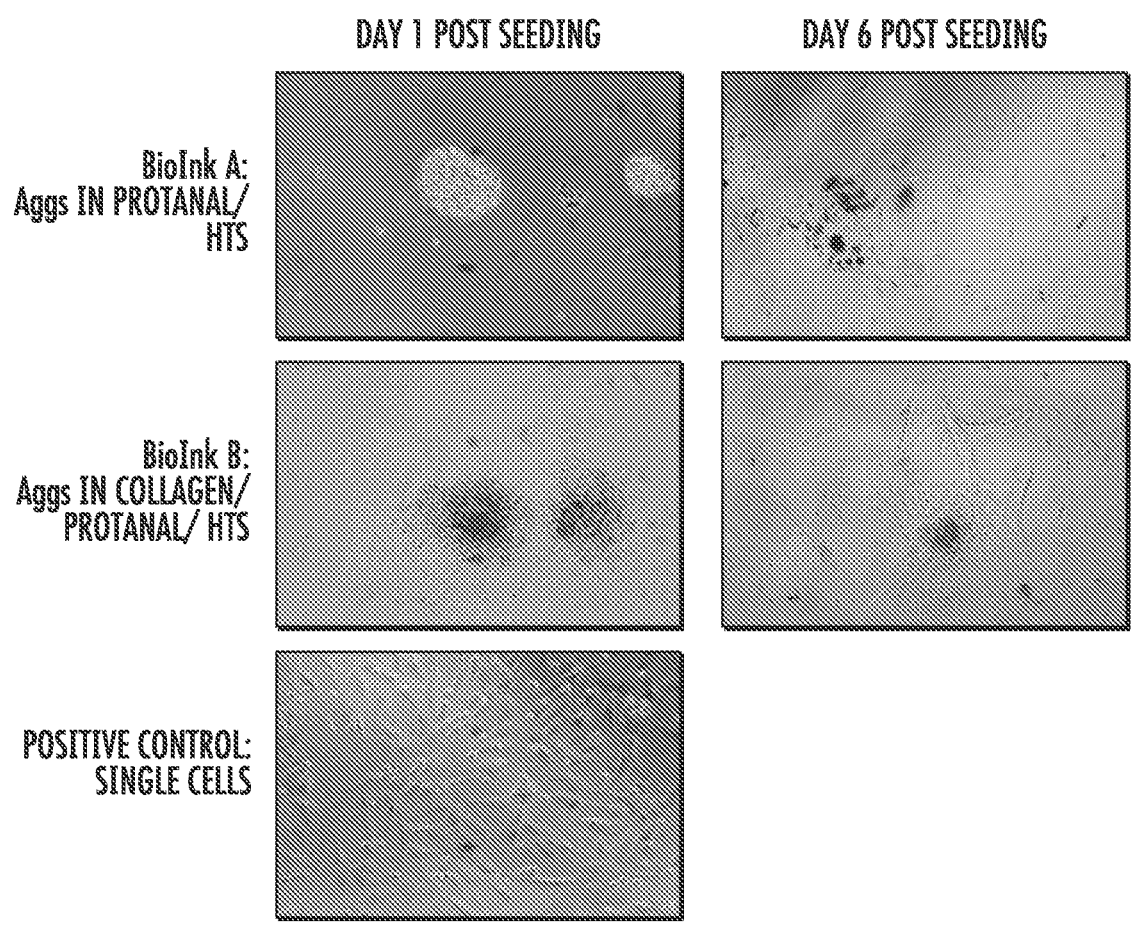
FIG. 23 is a series of images showing MSC aggregate survival in hydrogels after 7 days storage in 4° C. and expansion out of aggregates upon seeding onto TC plate.

MSCs attachment on TC culture plate was monitored and images taken on day 1 and day 6 post seeding (FIG. 23) where MSC aggregates in BioInk B were observed to attach onto TC plate to proliferate, demonstrating a highly feasible bioink formulation for the preservation of MSC aggregates. Printability of BioInk A and B were both tacky and strong, and 3D structure can be shaped with the partially solid gel.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An in vitro composition comprising:
   (a) a viscous matrix;
   (b) aggregates of viable mesenchymal stem cells (MSCs) suspended in said viscous matrix, wherein the aggregates contain on average 1,000-200,000 MSCs per aggregate, and wherein the composition comprises an overall average cell density of at least one million cells per milliliter; and
   (c) one of:
      (i) a biopreservative agent sold under the trade name Hypothermosol® in an amount effective to maintain the aggregates' ability to fuse following storage of the composition at 4° C. for 7 days, or
      (ii) a cryopreservative agent sold under the trade name Cryostor® in an amount effective to permit cryopreservation of the MSC aggregates in the composition.

2. The composition of claim 1, wherein the aggregates have a mean diameter variance less than 10% within the composition.

3. The composition of claim 1, wherein the viscous matrix comprises a biocompatible polymer.

4. The composition of claim 3, wherein the biocompatible polymer comprises a biopolymer.

5. The composition of claim 4, wherein the biocompatible polymer comprises a polysaccharide.

6. The composition of claim 5, wherein the biocompatible polymer comprises alginate.

7. A kit comprising:
   a. a composition comprising the composition of claim 1;
   b. a biocompatible polymer; and
   c. a crosslinking agent.

8. A closed system device comprising the composition of claim 1, wherein the closed system device is configured to dispense the composition as a discrete unit, wherein each discrete unit comprises controlled amounts of the cells.

9. The closed system device of claim 8, wherein the closed system device is a cartridge.

10. The closed system device of claim 8, wherein the closed system device is configured for use in a three-dimensional (3D) printer device.

* * * * *